United States Patent
Flores et al.

(10) Patent No.: US 10,492,356 B2
(45) Date of Patent: Dec. 3, 2019

(54) NONTOXIC COATING CONCENTRATES FOR AGRICULTURAL USES

(71) Applicant: CROP ENHANCEMENT, INC., San Jose, CA (US)

(72) Inventors: Jonathan Flores, Hyde Park, MA (US); Matthew A. Bosley, Watertown, MA (US); Sandra Rifai, Somerville, MA (US); Robert P. Mahoney, Newbury, MA (US); Damian Hajduk, San Jose, CA (US); Rosa Casado Portilla, Middleton, MA (US); Turner Newton, Somerville, MA (US); David S. Soane, Palm Beach, FL (US)

(73) Assignee: CROP ENHANCEMENT, INC., San Jose, CA (US)

( * ) Notice: Subject to any disclaimer, the term of this patent is extended or adjusted under 35 U.S.C. 154(b) by 0 days.

(21) Appl. No.: 15/641,897

(22) Filed: Jul. 5, 2017

(65) Prior Publication Data

US 2018/0020607 A1    Jan. 25, 2018

Related U.S. Application Data

(60) Provisional application No. 62/359,191, filed on Jul. 6, 2016, provisional application No. 62/404,343, filed on Oct. 5, 2016.

(51) Int. Cl.
*A01N 25/00* (2006.01)
*A01C 1/06* (2006.01)
*A01N 25/32* (2006.01)

(52) U.S. Cl.
CPC ............ *A01C 1/06* (2013.01); *A01N 25/32* (2013.01)

(58) Field of Classification Search
CPC .......................... A01N 25/30; A01N 25/00
See application file for complete search history.

(56) References Cited

U.S. PATENT DOCUMENTS

| | | | |
|---|---|---|---|
| 5,910,509 A * | 6/1999 | Broedel | A01N 43/16 514/291 |
| 6,451,731 B1 | 9/2002 | Agbaje et al. | |
| 6,743,756 B2 * | 6/2004 | Harris, Jr. | A01N 25/04 106/17 |
| 7,129,271 B2 | 10/2006 | Maupin et al. | |
| 7,371,444 B2 | 5/2008 | Kajikawa | |
| 9,161,532 B2 | 10/2015 | Devisetty et al. | |
| 2006/0154824 A1 * | 7/2006 | Yoshii | A01N 47/36 504/211 |
| 2007/0275258 A1 | 11/2007 | Ohnishi et al. | |
| 2010/0331187 A1 | 12/2010 | Williams et al. | |
| 2011/0166023 A1 | 7/2011 | Nettleton-Hammond et al. | |
| 2011/0274912 A1 | 11/2011 | Nakao et al. | |
| 2012/0071320 A1 * | 3/2012 | Atkinson | A01N 25/04 504/103 |
| 2015/0004102 A1 | 1/2015 | Salman et al. | |
| 2016/0088835 A1 | 3/2016 | Castelani | |
| 2016/0183538 A1 | 6/2016 | Taghavi et al. | |

FOREIGN PATENT DOCUMENTS

| | | |
|---|---|---|
| CN | 103733924 A | 4/2014 |
| WO | 2012/101660 A1 | 8/2012 |
| WO | 2016/035090 A1 | 3/2016 |

OTHER PUBLICATIONS

Machine translations and claims translation for CN103733924 obtained from Google Patents and Morningside Translations.

* cited by examiner

*Primary Examiner* — Johann R Richter
*Assistant Examiner* — Danielle Sullivan
(74) *Attorney, Agent, or Firm* — Elmore Patent Law Group, P.C.; Mahreen Chaudhry-Hoda; Carolyn S. Elmore

(57) ABSTRACT

The invention encompasses a nontoxic agricultural formulation of a concentrated liquid suspension comprising an organic phase and suspended particulate materials, and also encompasses an aqueous formulation comprising the concentrated liquid suspension and an agricultural treatment agent. The invention additionally encompasses methods of treating an agricultural target, comprising providing an agricultural formulation of a concentrated liquid suspension comprising an organic phase and suspended particulates, and applying the agricultural formulation onto the agricultural target, thereby treating the agricultural target.

22 Claims, No Drawings

NONTOXIC COATING CONCENTRATES FOR AGRICULTURAL USES

RELATED APPLICATIONS

This application claims the benefit of U.S. Provisional Patent Application No. 62/359,191 filed Jul. 6, 2016, and U.S. Provisional Patent Application No. 62/404,343, filed Oct. 5, 2016. The entire contents of the above applications are incorporated by reference herein.

FIELD OF THE APPLICATION

This application relates to coating formulations for agricultural uses.

BACKGROUND

Agricultural chemicals used as fertilizers, pesticides, herbicides, and the like, are prone to erosion and leaching from treated soils and plants. For example, fertilizers that are applied to fields can suffer run-off or loss caused by rapid watering, rain, or other water exposures. As another example, chemicals that are applied to foliar surfaces are prone to loss due to erosion from treated plants. As yet another example, pre-emergent agents (i.e., those agents that are applied to the soil before the germination of plants or weeds) need to stay where they are applied for a period of time while the plants and/or weeds are germinating. Dissipation of a pre-emergent agent by microbial activity, photodegradation, chemical degradation, run-off by water exposure, and the like, is undesirable during the germination period, and it is advantageous that the agent be retained in the top one or two inches of soil during this period. These problems are especially important for optimizing the properties of agents that need to act over a prolonged period of time to obtain their desired effect, as opposed to those agents that exert their effects immediately, like, for example, a pesticide that kills on contact. Without improved retention properties, agricultural chemicals can be washed off with rain or can be wiped off too easily.

As an example, protection of pre-harvest fruits/nuts/vegetables is of paramount importance. Growing fruits or vegetables on the trees and vines and bushes are prone to pest infestation and their tender skins are prone to sunburns reducing the overall yield of these products. In new farming methods, there is a push to reduce or eliminate the amount of synthetic pesticides that are used, particularly on fruits or vegetables with edible skins. To help overcome pest problems, these fruits or vegetables are often sprayed with particles capable of forming a barrier layer to prevent pest infestation and to prevent sunburns. In some other fruits such as cherries and tomatoes, even accumulation of water at the stems of the fruit leads to imbibition of water leading to osmotic imbalance inside the fruit resulting in unsightly cracking of fruit skin. To prevent this, there is a need for a breathable, benign and rainfast barrier coatings. There remains a need in the art for nontoxic alternatives to the use of pesticides to protect agricultural materials from insects, fungi, animals, drought conditions, air pollution damage, and solar damage. Furthermore, a need exists to improve herbicide performance by (1) enhanced retention of the active ingredients in the topsoil, (2) prevention of active ingredient leaching (i.e., sustained release) and (3) protection of the herbicides against photodegradation. There is a particular need for pre-harvest fruit/nut/vegetable protection because of the high value of these crops and the demand for organic produce.

A new generation of herbicides and other such agricultural treatment agents are biologically derived. For example, there are biological control agents that require delivery to agricultural targets, where retention and/or controlled release of those agents in proximity to the agricultural target is desired. As used herein, the term "agricultural target" is selected from the group consisting of a leaf, a fruit, a vegetable, a seed or seed case, a stem, a post-harvest agricultural product, and a soil, agricultural growth medium, or other agricultural substrates as would be understood by those of ordinary skill in the art. Desirably, a delivery formulation providing improved retention properties would be suitable for use with biological control agents.

Herbicides, insecticides, fungicides, plant growth regulators, insect pheromones, nutrients and other agricultural treatment agents are also advantageously used in spraying fruits or vegetables and plants directly. For example, cocoa pods can be afflicted by "black pod" disease, treated by spraying the pods with both fungicides and insecticides. Black pod is a plant disease caused by *Phytophthora* type oomycetes such as *Phytophthora infestans*, the pathogen that caused the Irish potato famine. Enhanced retention of the treatment agents on the target (e.g., the cocoa pod) can improve their efficacy and improve the efficiency of treatment protocols. A naturally derived coating for the cocoa pods could also create a physical barrier (i.e., a barrier coating composition, formed for example as a film) to deter pests, and could reduce or eliminate the need for additional treatment agents.

Agricultural treatment agents (pesticides, fertilizers, plant growth regulators, and the like) are costly and can cause environmental damage if misused. There is a need for materials and methods to improve the efficiency and costs associated with the use of agricultural treatment agents, or to reduce or eliminate the need for agricultural treatment agents.

SUMMARY

Disclosed herein, in embodiments, is a nontoxic agricultural formulation of a concentrated liquid suspension comprising an organic phase and suspended particulate materials. In embodiments, the formulation forms a cured coating on an agricultural target. In embodiments, the curing is water-resistant, resistant to friction, or rainfast. In embodiments, the cured coating retains the suspended particulate matters on the agricultural target when subject to an adverse condition, where the adverse condition can be a condition such as rainfall, friction, wind, water exposure, and secondary agricultural treatment. In embodiments, the formulation is stable against phase separation. In embodiments, the formulation comprises food grade ingredients, or comprises organically produced ingredients, or comprises ingredients generally recognized as safe. In embodiments, the formulation consists essentially of organically produced ingredients, or consists essentially of ingredients generally recognized as safe. In embodiments, the concentrated liquid suspension contains only non-aqueous liquids. The organic phase of the formulation can be about 40 to about 99% by weight of the formulation. The organic phase can comprise a drying oil, and the drying oil can be selected from the group consisting of linseed oil, raw linseed oil, boiled linseed oil, castor oil, castor oil glycidyl ether, tung oil, poppy seed oil, grapeseed oil, safflower oil, linoleic acid, linolenic acid, oleic acid, salicornia oil, sunflower oil, evening primrose oil, perilla oil and walnut oil. In embodiments, the drying oil comprises α-linolenic acid, linoleic acid, or a combination thereof. In embodiments, the suspended particulates are about 0.5 to about 50% of the formulation. The suspended particulates can be durably suspended in the organic phase or easily resuspended in the organic phase. In embodiments, the suspended particulates are selected from the group consisting of clay minerals and organically modified minerals. The clay minerals can be selected from the group consisting of kaolin clays, smectite clays, illite clays, chlorite clays, sepiolite, and attapulgite. In embodiments, the clay mineral can be a bentonite clay. In embodiments, the organically modified mineral is a clay mineral, and the organically modified mineral can be modified with an organic modifier selected from the group consisting of a fatty acid, fatty amine, fatty amide, fatty ester, fatty amine quat, quaternary amine surfactant, cetyltrimethylammonium bromide, fatty alcohol, decyl alcohol, dodecyl alcohol, linseed oil, alkenyl succinic anhydride, styrene maleic anhydride copolymer, colophony, rosin, chitosan, and a castor oil derivative. In embodiments, the formulation further comprises a pesticide, herbicide, beneficial bacterium, beneficial fungus, plant growth regulator, pheromone, sunscreen, biopesticide, or nutrient. In embodiments, the formulation further comprises a botanical extract or a plant oil. In embodiments, the formulation further comprises an additional particulate material. In embodiments, the additional particulate matter can be selected from the group consisting of talc, calcium carbonate, gypsum, magnesium silicate, calcium silicate, corn starch, cellulose fibers, psyllium fibers, ethylene bis stearamide, microcrystalline cellulose, stearic acid, oleic acid, wax, carnauba wax, and beeswax, or it can be kaolin or titanium dioxide. In embodiments, the formulation further comprises a surfactant. The surfactant can be selected from the group consisting of anionic, cationic, nonionic, biodegradable, food grade and organic surfactants. In embodiments, the formulation further comprises an adjuvant selected from the group consisting of cellulosics, polylactic acid, polyglycolic acid, and polylactic-glycolic acid. In embodiments, the formulation further comprises a salt or a curing additive.

Further disclosed, in embodiments, is an aqueous formulation comprising the concentrated liquid suspension of as described above and an agricultural treatment agent. Also disclosed, in embodiments, is a coated agricultural treatment agent comprising an agricultural treatment agent and the concentrated liquid suspension as described above, wherein the concentrated liquid suspension is applied to the agricultural treatment agent as a coating. In addition, disclosed herein are embodiments of a plant product having a surface treated with the formulation as described above.

Disclosed herein, in embodiments, are methods of treating an agricultural target, comprising providing an agricultural formulation of a concentrated liquid suspension comprising an organic phase and suspended particulates, and applying the agricultural formulation onto the agricultural target, thereby treating the agricultural target. In embodiments, the method protects the agricultural target from a pest or from environmental damage. In embodiments, the treatment comprises non-lethally altering the behavior of the pest. In embodiments, the agricultural target is a soil surface or an agricultural growth medium. In embodiments, the soil surface is treated to produce a beneficial effect selected from the group consisting of erosion control, nutrient retention, agricultural treatment agent retention, dust control, delivery of beneficial microbes, delivery of biopesticides, or augmentation of beneficial microbial growth. In embodiments, the agricultural target is a plant surface. The plant surface can be selected from the group consisting of leaves, fruits, seeds, berries, nuts, grains, stems, and roots. The plant surface can be a harvested product surface for a harvested product. In embodiments, the agricultural target is an agricultural growth medium. In embodiments, the agricultural formulation is applied to the agricultural target at a dosing rate of about 1 to about 200 lbs. of formulation per acre of crop. In embodiments, the agricultural formulation is diluted with a solvent prior to the step of applying the formulation. Further disclosed herein are methods for reducing spore-based transmission of a fungal plant disease by treating a plant surface with the formulations as described above, wherein the fungal plant disease is caused by a disease-causing fungus spore, and wherein contact with the formulation interferes with capacity of a disease-causing fungus spore to become airborne, thereby reducing spore-based transmission of the fungal plant disease. Also disclosed herein are methods of reducing spore-based transmission of a fungal plant disease by applying the formulations as described above to a plant surface, wherein the fungal plant disease is caused by a disease-producing fungal spore, and wherein contact with the formulation interferes with the ability of the disease-producing fungal spore to germinate on the plant surface, thereby reducing spore-based transmission of the fungal plant disease. Also disclosed herein are methods of treating a plant infection by applying the formulations as described above to a plant surface in need thereof. Such methods of treating comprise preventing the infection.

DETAILED DESCRIPTION

The present disclosure relates to nontoxic agricultural formulations in the form of a concentrated liquid suspension, where the formulation can form a cured coating on an agricultural target. The concentrated liquid suspensions of nontoxic agricultural formulations can be diluted in water to make solutions of the agricultural formulation for application by spraying, brushing, dipping, broadcasting, or irrigating. The agricultural formulations can be applied to a variety of agricultural substrates or targets, such as agricultural surfaces, including plant surfaces (leaves, fruits, seeds, berries, nuts, grains, stems, roots, etc.), soils or agricultural growth media, and harvested plant products such as fruits, vegetables, seeds, grains, stems, roots, and the like. As used herein, a plant surface is a surface of plant whether pre- or post-harvest; a plant product is a post-harvest agricultural product. Agricultural formulations and methods for treating agricultural substrates and targets are disclosed herein.

A. Agricultural Formulations

In embodiments, the nontoxic agricultural formulations comprise a plant oil that contains fatty acid or fatty ester functional groups that have at least one degree of unsaturation, such as monounsaturated and polyunsaturated fats. In embodiments, the plant oil contains unsaturated fatty groups such as alpha-linolenic acid, linoleic acid, and oleic acid, where these fatty groups can be in the form of a fatty acid, fatty acid salt, fatty ester, triglyceride, diglyceride, monoglyceride, or fatty amide. In embodiments, the plant oil is a drying oil. As used herein, the term "drying oil" refers to a self-crosslinking oil consisting of glycerol triesters of fatty acids, or to the plant oils described herein. Drying oils are characterized by high levels of polyunsaturated fatty acids, especially alpha-linolenic acid. Examples include linseed oil (i.e., flax seed oil, including boiled linseed oil (BLO) and raw linseed oil (RLO)), tung oil, poppy seed oil, canola oil, sunflower oil, safflower oil, soybean oil, fish oil, hemp oil, corn oil, dehydrated castor oil, tall oil, perilla oil and walnut oil. As crosslinks develop between double bonds of neighboring chains in the presence of atmospheric oxygen, a polymer network is formed, and the oil cures or "dries." The drying oils by themselves form tough hydrophobic films, so they can be used to coat surfaces or particles to repel moisture. The drying oils, as disclosed herein, can also suspend particulate materials, for example, particulate minerals, either so that the particulate materials do not separate from the drying oil ("durable" suspension), or so that the particulate materials are easily resuspended in the drying oil if they initially separate out.

In embodiments, the oil phase of the concentrated liquid suspension comprises drying oils, waxes, cellulosics, linseed oil, boiled linseed oil, castor oil, castor oil glycidyl ether, magnesium stearate, linseed oil, tung oil, poppy seed oil, grapeseed oil, safflower oil, linoleic acid, linolenic acid, oleic acid, salicornia oil, sunflower oil, corn oil, hemp oil, wheat germ oil, cottonseed oil, soybean oil, sesame oil, canola oil, evening primrose oil, perilla oil and walnut oil. In embodiments, the oil phase of the concentrated liquid suspension contains diluents such as mineral oil, a petroleum distillate, an alcohol, a terpene, or a glycol such as glycerin or propylene glycol to improve fluid handling properties, or to improve the flexibility of the dried film. Preferably the oil phase contains α-linolenic acid, linoleic acid, or a combination thereof.

The concentrated liquid suspension contains particulate material in a plant oil. In embodiments, the particulate material can be a clay mineral. Clay minerals include, without limitation, the following types of clays: (a) kaolin clays (including the minerals kaolinite, dickite, halloysite, and nacrite (polymorphs of $Al_2Si_2O_5(OH)_4$); (b) smectite clays, including dioctahedral smectites such as such as nontronite and montmorillonite, and trioctahedral smectites such as saponite; (c) illite clays, which include the clay-micas; (d) chlorite clays, and (e) other clay types such as sepiolite and attapulgite. In an embodiment, the clay mineral can be a bentonite clay.

In embodiments, the particulate material can be an organically modified mineral such as an organoclay. For example, an organoclay can comprise a mineral such as a bentonite, kaolin, zeolite, attapulgite, or talc that is modified with an organic modifier such as a fatty acid, fatty amine, fatty amide, fatty ester, fatty amine quat, quaternary amine surfactant, cetyltrimethylammonium bromide, fatty alcohol, decyl alcohol, dodecyl alcohol, linseed oil, alkenyl succinic anhydride (ASA), styrene maleic anhydride (SMA) copolymer, colophony, rosin, chitosan, or a castor oil derivative such as THIXCIN®.

In embodiments, the particulate material can be talc, calcium carbonate, gypsum, magnesium silicate, calcium silicate, corn starch, cellulose fibers, psyllium fibers, ethylene bis stearamide, microcrystalline cellulose, stearic acid, paraffin wax, carnauba wax, or beeswax, with particulate materials used either individually or together as mixtures. In other embodiments, the particulate material can be a specialized particle that is chosen to form barriers, for example, against moisture or pest infestation. In embodiments, specialized particles can comprise planar high-aspect-ratio particles such as clays, mica, and the like, that have the ability to form a flat organized film when mixed with suitable binders. In certain embodiments, the particulate material of the formulation can be a non-clay mineral such as mica, talc, silica, titanium dioxide, gypsum, calcium carbonate, aluminum phosphate, and the like. In preferred embodiments, the particulate material of the formulation can be bentonite, exfoliated bentonite, organoclays, kaolin, gypsum, zeolite, fuller's earth, or diatomaceous earth.

In embodiments, clay for these applications can be exfoliated by use of the methods set forth in WO2013/123150 (PCT Application No. PCT/US13/2684 entitled "Processes for Clay Exfoliation and Uses Thereof"), the contents of which are incorporated herein by reference. The incorporation of particles in the barrier films provides additional benefits of reflecting or absorbing light and heat energy. Certain fruits and vegetables are subject to crop losses or economic damage due to exposure to environmental stresses like excessive sunlight, freezing or frost conditions, oxidative damage, microbial or fungal growth, osmotic swelling and cracking during wet conditions, heat stress, and desiccation during low humidity or windy conditions. The incorporation of particles in the barrier films of the disclosed formulations can reduce the damages caused by these stresses. These particles can be combined with additional high brightness pigments such as titanium dioxide ($TiO_2$) to provide a white or a reflective surface that lowers heat absorption from sunlight and thereby reducing sunburn-induced or heat-induced damage. $TiO_2$ can additionally enhance the ultraviolet (UV) light resistance of the agricultural target surface by absorbing or reflecting the majority of the UV radiation incident on the agricultural target surface. Other sunscreen materials such as conjugated organic compounds may also be included.

The agricultural formulations are provided in the form of a concentrated liquid suspension comprising an oil-based continuous phase and suspended particulates. The concentrated suspension is a liquid with a viscosity between about 10 cP and about 50,000 cP, as measured by a Brookfield LVDV-III+ Rheometer with spindle LV-3 at 30 rpm; alternatively, the concentrated suspension is a paste-like fluid with a viscosity between about 50,000 cP and 500,000 cP, as measured by the same instrument under the same conditions. In embodiments, the concentrated suspension is a liquid with a viscosity between about 50 cP and about 5000 cP. In embodiments, the concentrated suspension is stable against separation of the particulates from the oil based continuous phase (i.e., phase separation), such that the suspension resists sedimentation for at least 24 hours after it is mixed. In embodiments, the suspension resists sedimentation for at least 90 days after it is mixed. In embodiments, the concentrated suspension contains more oil based liquid than suspended particulates on a mass basis. In embodiments, the mass ratio of particulates to oil based liquid in the formulation is in the range of 1 to 100 parts of particulates per 100 parts of oil based liquid. In embodiments, the concentrated liquid suspension is free of water.

In embodiments, the agricultural formulation comprises surfactants to improve dispersibility of the particulate minerals in the oil phase and to improve the wetting of the diluted formulation on an agricultural target. As would be understood in the art, particulate materials such as minerals can be hydrophilic in nature, so that they do not readily become suspended in an oil. In embodiments, therefore, the formulation contains a surfactant or dispersant such as an ethoxylated alcohol, a sorbitan fatty ester, an alkylpolyglycoside, an ethylene oxide/propylene oxide (EO/PO) copolymer, guar, xanthan, soy lecithin, or an ethoxylated sorbitan stearate, which is understood to facilitate the stable suspension of the particulate minerals in the oil phase, allowing a durable and stable concentrated liquid formulation.

In embodiments, the agricultural formulation comprises dispersants or suspending agents to improve dispersibility and dilutability of the formulation into water, to improve the stability of the diluted formulation, and to improve the wetting of the diluted formulation on an agricultural target. In embodiments, the concentrated liquid suspension contains a dispersant or suspending agent such as guar, xanthan, carboxymethylcellulose, carrageenan, alginate, gelatin, pectin, starch, hydroxypropylguar, hydroxypropylcellulose, hydroxypropylmethyl cellulose, hydroxypropylethyl cellulose, hydroxyethylcellulose, and ethylcellulose. In embodiments, the dispersant or suspending agent is added to the agricultural formulation at about 0.01% to about 5% on a weight basis. In embodiments, the dispersant or suspending agent is added to the agricultural formulation at about 0.1% to about 2% on a weight basis. In embodiments, the dispersant or suspending agent is added to the agricultural formulation at about 0.1% to about 1% on a weight basis.

In embodiments, the agricultural formulation comprises one or more stabilizing additives, which may be added in amounts ranging from 0.1 wt % to 30 wt %, depending on the additive.

Without being bound by theory, it is understood that, because the formulation comprises domains of high-density material dispersed in a continuous domain of low-density material, gravitational forces can drive the high-density material to settle on the bottom of the container and form sediment. To counter this, stabilizing additives can be employed to increase the viscosity of the continuous phase, thereby reducing the sedimentation rate, but these render the formulation difficult for the users to pour. As an alternative, additives can be selected that cause the continuous phase to exhibit pseudoplastic behavior, i.e., where the viscosity decreases with increasing shear rate. A formulation containing such additives exhibits a reduced sedimentation rate but can still be poured easily, since the shear rate characteristic of sedimentation is considerably less than that of pouring, mixing, or other fluid transfer processes.

In embodiments, stabilizing additives can be selected that cause the continuous phase to form a fragile solid at low shear stresses that transforms into a liquid once a critical stress level is exceeded. The composition and concentration of such an additive is chosen such that the critical stress is slightly greater than the shear stress associated with sedimentation. A formulation containing such additives exhibits essentially no sedimentation, but flows freely once the fragile solid is disrupted by shaking, mixing, or other forms of gentle agitation. In embodiments, stabilizing additives producing this behavior comprise one or more macromolecules that contain weakly associating groups. Interaction among these weakly-associating groups leads to the formation of a network structure that extends throughout the formulation and is characterized by a yield stress. Desirably, applied shear stresses that exceed the yield stress disrupt these associations, resulting in the collapse of the network and the macroscopic flow of the formulation.

In embodiments, additives especially suitable for manifesting these properties include nonionic triblock copolymers, such as poloxamers, composed of a central hydrophobic chain (e.g., polyoxypropylene) between two hydrophilic chains (e.g., polyoxyethylene), for example, those provided by the PLURONIC® series of materials (BASF), and polyether amines, such as the polyether diamines in the JEFFAMINE® ED series (Huntsman). In other embodiments, useful stabilizing additives can include castor oil derivatives such as trihydroxystearin and related rheology modifiers (THIXCIN® and THIXATROL® (Elementis Specialties)), or RHEOCIN® or RHEOCIN T® (BYK Additives and Instruments). Additives for these purposes can be added at doses ranging from 0.01 to 1 wt %, preferably from 0.05 to 0.3 wt %. In embodiments, the stabilizing additive can be added to the agricultural formulation at an elevated temperature relative to that of the formulation while mixing with high intensity, for example at a temperature ranging from 55 to 65° C.

In embodiments, stabilizing additives can include modified urea, urea-modified polyamides, urea-modified polyurethanes, hydroxyl-terminated polybutadiene resins (KRASOL® (Cray Valley)), glycol ethers (e.g., the DOWANOL™ series (Dow Chemical)), polyamides, polyester amides, and the like. As examples, compounds such as the BYK® products: BYK 7411 ES, BYK 431, BYK 430 and BYK 425 (BYK Additives and Instruments) can be used. These additives can be incorporated in the system at a concentration ranging from 0.1 to 4 wt % and preferably form 0.2 to 2 wt %. In embodiments where glycol ethers are used (e.g., the DOWANOL™ series (Dow Chemical)), the selected glycol ethers will preferably have a high solubility in water. As an example, the Dowanol TPM can be used at a dose ranging from 3 to 5 wt % and preferably 4 wt %. In other embodiments, stabilizing additives can include surfactants derivatized from fatty acids such as fatty acid polydiethanolamide: examples of these are cocamide diethanolamine, lauramide diethanolamine, soyamide diethanolamide and the like, representative versions of which can be found in the AMIDEX™ CE, KD, LSM products from Lubrizol. In other embodiments, surfactants derived from fatty acids such as the polyglycerol esters of fatty acids can be used as stabilizing additives. These fatty-acid derived additives can be added at a dose ranging from 1 to 5 wt % and preferably 3%.

In embodiments, the agricultural formulations comprise biodegradable ingredients, or consist essentially of biodegradable ingredients. In embodiments, the agricultural formulations comprise organically produced, or "organic" ingredients as defined in the United States Department of Agriculture (USDA) National Organic Program (NOP) ingredients list. In embodiments, the agricultural formulations comprise food grade ingredients as defined by the United States Food and Drug Administration (FDA) guidelines. In embodiments, the agricultural formulations comprise inert ingredients as defined in the United States Environmental Protection Agency (EPA) Inert Ingredients List in 40 CFR180 paragraphs 910-960. In embodiments, the agricultural formulations comprise FIFRA Minimal Risk ingredients as defined in 40 CFR 152.25, under the United States Federal Insecticide Fungicide and Rodenticide Act (FIFRA). In embodiments, the agricultural formulations are nontoxic, naturally derived, and/or organic, and the formulations can be used to prevent damage to crops by insects, animals, fungi, bacteria, and environmental damage. In embodiments, the formulation ingredients are derived from food grade raw materials. In embodiments, the formulation ingredients comprise materials generally recognized as safe ("GRAS") by the U.S. Food and Drug Administration, as set forth in 21 CFR 170.3 and 21 CFR 170.30, under the Federal Food, Drug, and Cosmetic Act (FDCA), sections 201(s) and 409, or consist essentially of materials generally recognized as safe.

This concentrated liquid suspension has a number of commercial advantages, for example a highly concentrated product form minimizes the volume of product to be shipped from the point of manufacture to the point of use. The storage capacity requirements are minimized by having a highly concentrated product form. It also offers advantages over the solid, granular or powdered formulations: ease of handling as liquid product, compatibility with automated pumping equipment, safer for handling with reduced worker exposure, and less dust formation. The minimal amount of water in the product can provide benefits in lowered viscosity, reduced tendency for mold and bacteria growth, and a lower freezing point or pour point of the product.

In certain embodiments, the concentrated liquid suspension can be diluted with water or with other solvents at or near the point of use to form a diluted liquid suspension, and the diluted liquid suspension can then be applied to an agricultural target by methods such as spraying, misting, fogging, electrostatic spraying, dipping, brushing, or broadcasting. The dilution can be accomplished by inline mixing or batch mixing to form the diluted suspension, and the diluted suspension can be handled and applied using conventional spraying equipment. The diluted suspension is formed as an oil-in-water emulsion or an oil-in-water suspension, where the oil phase comprises the drying oil.

When applied to an agricultural target, the agricultural formulation forms a curable coating comprising the oil and the particulate material. In embodiments, the curing mechanism is based on the behavior of the drying oil, where crosslinks develop between double bonds of neighboring fatty acid or triglyceride chains via atmospheric oxygen insertion, forming a cured polymer network. The rate of curing can be increased by use of curing additives, i.e., additives such as oxidants or metal salts that accelerate the rate of curing of the drying oil.

In embodiments, the concentrated suspension is made by blending a surfactant, a drying oil, and particulates, where the surfactant represents about 0.1 to about 15% by mass of the suspension. In an embodiment, the suspension contains no water. In embodiments, the suspension contains less than 20% water by mass. In embodiments, the concentrated suspension contains from about 40% to about 98% by mass of an oil phase. In embodiments, the concentrated suspension contains from about 50% to about 90% by mass of an oil phase. In embodiments, the concentrated suspension contains from about 60% to about 80% of an oil phase. In embodiments, the concentrated suspension contains from about 1% to about 50% by mass of suspended particulates. In embodiments, the concentrated suspension contains from about 10% to about 40% by mass of suspended particulates. In embodiments, the concentrated suspension contains from about 20% to about 35% by mass of suspended particulates.

In embodiments, the agricultural formulations comprise or consist essentially of ingredients that are nontoxic, such that they have a low toxicity towards plants or animals. Low toxicity can be defined as having a $LD_{50}$ of >1000 mg/kg, or preferably a $LD_{50}$ of >5000 mg/kg. Toxicity has been classified by Hodge-Sterner classes, based on article "Tabulation of Toxicity Classes" by Harold Hodge and James Sterner, published in American Industrial Hygiene Association Quarterly Volume 10, Issue 4, 1949. In embodiments, the agricultural formulations can fit the description of Hodge-Sterner classes 1, 2, or 3; in preferred embodiment, the formulations can fit the description of Hodge-Sterner class 1. In embodiments, the agricultural formulations comprise naturally derived ingredients, such as plant oils, triglycerides, and naturally occurring minerals.

In embodiments, the agricultural formulations can be applied such that they dry into the form of a porous film, allowing for transpiration by the plant. In embodiments, the porous film can be formed by incorporating or forming micropores in the form of gas voids, or by incorporating porous minerals. In embodiments, the micropores can be formed by dissolution or degradation of a minor component of the coating, leaving behind a porous coating.

In embodiments, the agricultural formulations disclosed herein can be used as vehicles or adjuvants for conveying agricultural treatment agents in fluid form to agricultural targets. As used herein, the term "treat" means to beneficially affect the longevity, productivity, or other biological or economic aspect of an agricultural target, and an "agricultural treatment agent" refers to any chemical or biological active ingredient used to carry out such treatments. The term "secondary agricultural treatment" refers to an agricultural treatment that is applied in addition to, before, or subsequent to a treatment with the agricultural formulations disclosed herein. Non-limiting examples of agricultural treatment agents include pesticides, herbicides, fungicides, sulfur, copper oxide, plant growth regulators, plant hormones, pheromones, insecticidal soaps, insect pheromones, sunscreens, beneficial bacteria, beneficial fungi, *Trichoderma*, *Bacillus thuringiensis* (Bt), *Aspergillus*, nematodes, RNAi; Botanical extracts and essential oils such as neem, clove, d-limonene, citrus extract, pinene, pine extract, capsaicin, camphor, geraniol; probiotics, beneficial bacteria or beneficial fungi, extracts from bacterial cultures or fungal cultures, Spinosyn A, Spinosyn D, biopesticides, biofungicides, nematodes, biological control agents, and nutrients.

As used herein, the term "nutrient" or "nutrients" refers to those elements that are essential to plant growth. The term "nutrients" includes both macronutrients and micronutrients. Besides the essential elements for growth provided by air and water (carbon, hydrogen, oxygen), there are the three macronutrients (nitrogen, phosphorus, potassium) that plants require in large quantities, and a number of secondary nutrients and micronutrients (calcium, magnesium, sulfur, boron, chlorine, copper, iron, manganese, molybdenum, zinc, and the like) that are required in smaller, even trace, amounts. The micronutrients can perform especially critical functions in the plant lifecycle, such as enhancing sugar translocation, strengthening protein formation, increasing photosynthesis, improving root strength, enabling plant immunity, and the like.

Nutrient-containing foliar sprays can be used to provide essential nutrients to plants, for example to correct nutritional deficiencies that limit plant growth or increase susceptibility to pests and pathogens. However, simple sprays that are currently in use consist of one or more nutrients dissolved or dispersed in water; after application, these formulations are easily washed or brushed off the foliar surface. This susceptibility to wash-off or brush-off decreases nutrient availability, and it can add to the run-off of these chemicals into local water supplies. In embodiments, the formulations disclosed herein contain nutrients, and form a nutrient-containing film that retains one or more nutrients on the foliage. This property minimizes nutrient wash- or brush-off, extending the time available for absorption by the plant and extending the residual activity of the nutrient. Examples of suitable nutrients include nitrogen, phosphorus, potassium, boron, copper, iron, manganese, molybdenum, zinc, chlorine, nickel, calcium, magnesium, sulfur, and silicon. Nutrients may be supplied as salts, complexes, chelates, or organic-inorganic compounds. Nutrients may be dissolved in the formulation, dispersed in the formulation, or adsorbed to a component of the formulation. In embodiments, for example, nutrients may be adsorbed to the clay present in the formulation. Dispersed nutrients may take the form of particles with a mean particle size of less than 100µ, less than 10µ, or less than 1µ.

In embodiments, the nontoxic agricultural formulation can be combined with a pheromone that causes mating confusion in insects. The pheromone-containing agricultural formulation can be used to deter successful insect reproduction or oviposition, or to cause insects to deposit eggs in areas where the resulting larvae will not survive. Agricultural treatment agents can comprise agricultural chemicals that may be formulated as liquids, solutions, dispersions, pastes, gels, or aerosols. Agricultural treatment agents can non-lethally alter the behavior of a pest. For example, agricultural treatment agents can comprise biological control agents, which exert a beneficial effect on an agricultural target through their biological activity, for example, by competing with agricultural pathogens for space or nutrient on the agricultural target, or by antagonizing the growth of agricultural pathogens, by inducing resistance in the agricultural target, by acting as a natural enemy to an agricultural pest, by causing mating confusion, by causing excessive grooming behavior, or by other biologically-mediated processes. As used herein, an agricultural target can include plant surfaces and seed surfaces (pre- or post-harvest), plant products, and soil or agricultural growth media surfaces.

As used herein, the term "agricultural chemical" refers to an active chemical ingredient used for agricultural purposes, such as an herbicide, pesticide, fungicide, fertilizer, insecticide, probiotic, nematicide, plant growth regulator, plant hormone, insect hormone, pheromone, pest repellent or nutrient. For example, the formulation can serve as a protective coating for plants, fruits, vegetables, foliage, berries, seeds, nuts, and the like, while also delivering an agricultural chemical. In embodiments, the agricultural chemicals can be herbicides such as dicamba, chloramben, nicosulfuron, and glyphosate; they can be insecticides such as imidacloprid, neonicotinoids, pyrethroids, chlorantraniliprole, or sulfoximines. In embodiments, the agricultural chemicals can be fungicides such as azoxystrobin, calcium polysulfide, Metalaxyl, chlorothalonil, fenarimol, copper salts, cuprous oxide, metal-dithiocarbamate complexes, ferbam, mancozeb, mefenoxam, myclobutanil, pyraclostrobin, prothioconazole, propiconazole, sulfur, thiophanate methyl, triadimefon, and trifloxystrobin. In embodiments, the agricultural chemical can be an oil-soluble chemical, a water-soluble chemical, or a dispersible solid material.

In embodiments, the agricultural treatment can be a physical agent such as a sunscreen or a moisture retainer. In embodiments, agents such as caffeine, benzoic acid, para-amino benzoic acid, avobenzone, zinc oxide, and titanium dioxide can be used as sunscreens. In embodiments, humectant agents such as urea, glycerol, polyvinylalcohol, ethylcellulose, methylcellulose, hydroxyethylcellulose, calcium chloride, and polyethylene glycol (PEG) can be used as moisture retainers.

In embodiments, the agricultural treatment agent can comprise a biological agent such as gram-positive bacterium, a gram-negative bacterium, a motile microbe, a non-motile microbe, a root nodule microbe, a soil microbe, a rhizosphere microbe, a fungus, and the like.

In certain embodiments, the biological agent comprises one or more beneficial microbes. As used herein, the term "microbe" is interchangeable with "microorganism," referring to a microscopic single-celled or multicelled organism. Classes of microorganisms include, but are not limited to, organisms such as bacteria, fungi, algae, archaea, viruses, and protozoa. Use of microbes as agricultural treatment agents can offer agricultural benefits such as enhancing nitrogen fixation, suppression of disease, protection against plant pathogens, inducing disease-resistance in plants, improving nutrient uptake, stimulating growth and productivity, improving tolerance to environmental stress and the like. For example, in embodiments, microbes used for agricultural treatment can provide direct protection for a plant by infecting insect pests or plant-pathogenic microorganisms that may attack the plant. As an example of this use, *Beauveria bassiana*, a fungus naturally present in soils, may be used as an entomological pathogen against insect pests. Or, for example, in other embodiments, microbes used for agricultural treatment can provide indirect protection for a plant by competing with pathogenic species for nutrients, by restricting or eliminating nutrients required by pathogenic species or insect pests, or by producing antimicrobial compounds that adversely affect pathogenic species. In yet other embodiments, microbes used for agricultural treatment can increase the supply or bioavailability of nutrients to the plant. In other embodiments, microbes used for agricultural treatment can stimulate beneficial biological activity within the plant, for example, stimulating foliar growth, stimulating root growth, stimulating immune response, fostering tolerance of abiotic stress, and the like.

In embodiments, the agricultural treatment can comprise a biological agent such as beneficial bacteria or fungi, for example, fungi in mycorrhizal relationship with the roots of plants, entomopathogenic strains of fungi, *Beauveria, Metarhizium, Isaria, Nomuraea, Tolypocladium, Lecanicillium, Entomophthora muscae, Beauveria bassiana, Pandora neoaphidis, Hirsutella thompsonii, Neozygites floridana, Paecilomyces fumosoroseus, Metarhizium anisopliae, Bacillus aspergillus, Bacillus thuringiensis* (Bt), and nematodes. In embodiments, the agricultural treatment agent can be a biopesticide as defined by the United States EPA (https://www.epa.gov/pesticides/biopesticides). In embodiments, the agricultural treatment agent can be produced by bacteria, such as spinosyn A and spinosyn D, which are produced by *Saccharopolyspora spinosa*.

In embodiments, the formulation can comprise a beneficial microbe that is a viable microbe. A viable microbe can be a propagatable microbe, i.e., one that is a living organism capable of replication. Alternatively, the beneficial microbe can be viable but non-propagatable, having beneficial properties not dependent upon their replication. For these viable microbes, whether or not capable of replication, certain of their beneficial attributes can arise from their capacity to release beneficial substances that contribute to the well-being (including absence of disease) in a plant, or certain of their beneficial attributes can arise from their capacity to induce a plant-beneficial effect when consumed by another organism having a relationship to such plant. For example, the viable beneficial microbe, whether or not propagatable, can have an adverse effect on a pest that might otherwise infest a plant, for example if the pest consumes the microbe; this adverse effect on the pest thus has a beneficial effect on the otherwise vulnerable plant.

In embodiments, the formulation can comprise a beneficial microbe that is a non-viable microbe. Such microbes, while living organisms at some point, are no longer alive in the formulation, and their beneficial properties are not dependent upon their viability. The non-viable microbes or substances derived from them can exert beneficial effects, for example by providing beneficial substances that contribute to the well-being (including absence of disease) in a plant, or by inducing a plant-beneficial effect when consumed by another organism having a relationship to such plant. For example, a microbe such as *B. thuringesis* can damage the gut of insects that consume it, even if the microbe itself is no longer alive.

Non-viable materials, e.g., compounds derived from viable or non-viable microbes, can be included in the term "biopesticide." Such biopesticides can include materials (e.g., compounds, secretions, excretions, etc.) derived from living microbes; biopesticides can also include materials derived from non-viable microbes (e.g., compounds, secretions, excretions, or derivatives from processing the microbes themselves).

In embodiments, the concentrated liquid suspension can comprise adjuvants such as cellulosic polymers, cellulose acetate, cellulose acetate butyrate, cellulose acetate propionate, starch, thermoplastic starch, polyethyleneglycol, polylactic acid, polyglycolic acid, polylactic-glycolic acid, propylene glycol, block copolymers of ethylene oxide and propylene oxide, glycerin, osmotic suppressors such as calcium chloride, terpenes, and plant oils. In embodiments, the drying-oil based agricultural formulation can comprise a cellulose-based or cellulose-derived material such as cellulose esters, cellulose acetate, cellulose diacetate, cellulose triacetate, cellulose acetate propionate, cellulose acetate butyrate, cellulose fibers, cellulose microfibers, cellulose nanofibers, cellulose ethers, ethylcellulose, methylcellulose, carboxymethylcellulose, hydroxyethylcellulose, hydroxypropylcellulose, hydroxypropylmethylcellulose, and the like. In embodiments, the cellulose-based or cellulose-derived material can be a cellulose-based polymer that has a drying oil covalently attached to it, for example by esterification. In embodiments, a cellulose-derived material can contain a cellulose-based material as described above combined with one or more functional groups that impart advantageous properties. In other embodiments, the nontoxic barrier coating composition for agricultural surfaces can be formed from a biodegradable composition comprising a polyhydroxyalkanoate such as polyhydroxybutyrate.

B. Methods of Using the Formulations

The present disclosure also relates to methods of using nontoxic agricultural formulations in the form of a concentrated liquid suspension. The agricultural formulations can be applied to a variety of agricultural substrates or targets, such as plant surfaces (leaves, fruits, seeds, berries, nuts, grains, stems, roots, etc.), soils or agricultural growth media, and harvested plant products such as fruits, vegetables, seeds, grains, stems, roots, and the like.

In embodiments, the soil surface can be treated to produce a beneficial effect selected from the group consisting of erosion control, nutrient retention, agricultural treatment agent retention, dust control, delivery of beneficial microbes, or augmentation of beneficial microbial growth.

In embodiments, the nontoxic agricultural formulations can be used to form seed coatings to improve properties of the seeds, such as viability, productivity, growth rate, emergence timing, insect resistance, mold resistance, dust control, resistance to flaking off of active pesticide ingredients, and moisture resistance. When used as seed coatings, the formulations can provide protection against *Rhizoctonia* and *Fusarium* and soybean rust and nematodes, aphids, maggots, and worms. The formulations can offer reduced dusting of seed coatings for handling improvements, safety, environmental contamination, and avoiding nontarget applications. The seed coatings can improve dry flow and non-clumping of the treated seeds; this results in less residue and requires less cleaning of equipment. Seed coatings can include rooting compounds, hormones and plant growth regulators. In embodiments, the formulation can be diluted with water and applied to an agricultural target to form a cured coating.

In embodiments, the nontoxic agricultural formulations can be applied to tropical crops such as cocoa, coffee, papaya, mango, pineapple, avocado, melons, watermelons, and banana. In the example of cocoa, the nontoxic agricultural formulation can deter cocoa pod borers (*Conopomorpha cramerella*) from damaging the crop. In addition, for cocoa, the nontoxic agricultural formulation can deter black pod infestations, for example involving *Phytophthora* species organisms such as *P. palmivora, P. megakarya, P. capsici, P. citrophthora, P. megasperma, P. katsurae*, and the like. Also, for cocoa, the nontoxic agricultural formulation can deter frosty pod and witches' broom disease (WBD) infestations, involving organisms such as basidiomycete fungi, *Moniliophthora roreri, Moniliophthora perniciosa*, and the like. In coffee, the nontoxic agricultural formulation can deter insects such as the coffee berry borer, or plant diseases such as coffee rust. In embodiments, the nontoxic agricultural formulation can prevent or reduce the spread of fungal infestations by reducing the ability of spores to become airborne. In embodiments, the nontoxic agricultural formulation can prevent or reduce the spread of fungal infestations by reducing the ability of airborne spores to germinate on plant surfaces. In embodiments, the nontoxic agricultural formulation can prevent or reduce the spread of fungal infestations by encapsulating or otherwise immobilizing fungi on plant surfaces, preventing part or all of the microorganism from obtaining access to the plant interior.

In embodiments, the nontoxic agricultural formulations can be applied to vegetable crops such as squash, onion, celery, lettuce, spinach, pumpkin, tomato, eggplant, peppers, broccoli, cabbage, cucumber, and the like. In embodiments, the nontoxic agricultural formulations can be applied to root crops such as potato, beet, carrot, turnip, ginger, and sweet potato. In embodiments, the nontoxic agricultural formulations can be applied to legume crops such as beans, soybeans, and peanuts. In embodiments, the nontoxic agricultural formulations can be applied to cereal grains such as corn, oat, wheat, sorghum, alfalfa, barley, and rice. In embodiments, the nontoxic agricultural formulations can be used to deter pests such as the corn earworm, navel orangeworm, and pecan case borer. In embodiments, the nontoxic agricultural formulations can be applied to tree nut crops such as almond, cashew, macadamia, walnut, pecan, and pistachio. In embodiments, the nontoxic agricultural formulations can be applied to tree fruits such as apples, pears, peaches, plums, cherries, lemons, oranges, grapefruits, pomelos, and limes. In embodiments, the nontoxic agricultural formulations can be applied to berry crops such as strawberries, raspberries, blueberries, cranberries, blackberries, and elderberries. In embodiments, the nontoxic agricultural formulations can be applied to grapes for production of table grapes, juice, or wine. In embodiments, the nontoxic agricultural formulations can be applied to turf grasses, lawns, golf courses, and ornamental plants.

In embodiments, the nontoxic agricultural formulations can be used to improve the yield of a crop. The yield of a crop is determined by numerous factors, including plant health, nutrient and water availability, pest pressures, heat stress, environmental conditions, sunlight, and the microbiome around the plants. When applied to a crop, the nontoxic agricultural formulation can influence certain of these factors. In embodiments, the nontoxic agricultural formulations can reduce the water demand of a crop by reducing the loss of water vapor by transpiration to the atmosphere.

In embodiments, the nontoxic agricultural formulations can be used to protect plants and crops from diseases caused by microorganisms, including, but not limited to, microorganisms such as fungi, mold, mildew, bacteria, viruses, and the like, causing diseases such as potato virus X (PVX), potato virus Y (PVY), blight, zebra chip disease, bacterial infections, phytoplasmas, leafspot, brown rot, gall, downy mildew, corn smut, apple rust, leaf curl, leaf spot, mosaic virus, oomycetes, mistletoe, dwarf mistletoe, scab, canker, anthracnose, and the like. In embodiments, the nontoxic agricultural formulations can be used to protect plants and crops from insect-borne bacteria and viruses. As used herein, the term "infection" refers to a pathological infestation of a plant by a microorganism, or a disease caused thereby. It is understood that an infection can result from an invasion of a plant by an exogenous source of microorganisms, where the attachment to or colonization of the plant by the microorganism results in plant pathology or disease, either by surface-directed activities, by entry of the exogenous microorganism into the plant interior, or by other pathogenic behaviors of the microorganism (e.g., toxin formation). It is also understood that an infection can occur due to an endogenous source of microorganisms that behaves in a pathological manner, either by surface-directed activities, by entry of the endogenous microorganism into the plant interior, or by other pathogenic behaviors of the microorganism (e.g., toxin formation). As an example, an infection can result when the microorganism is initially present on the plant surface (whether the microorganism is originally an exogenous one or an endogenous one), and entry of part or all of this microorganism into the plant interior results in the plant pathology. In certain embodiments, in preventing or ameliorating or eradicating infections (collectively, "treating infections"), the nontoxic agricultural formulation can encapsulate or otherwise immobilize the potentially pathogenic microorganisms on the plant surface, thereby preventing part or all of the microorganisms from obtaining access to the plant interior. In other embodiments, in treating infections, the non-toxic agricultural formulation can prevent the incursion of potentially pathological exogenous microorganisms onto the plant. In yet other embodiments, in treating infections, the nontoxic agricultural formulation can counteract or prevent surface-directed activities or other behaviors of microorganisms, such as toxin formation.

In embodiments, the nontoxic agricultural formulations can be used to protect plants and crops from insect and animal damage caused by weevils, maggots, worms, slugs, flies, fruit flies, mites, ants, spiders, caterpillars, moths, grasshoppers, locusts, leafhoppers, leafrollers, leafminers, aphids, psyllids, ants, beetles, bugs, thrips, rabbits, deer, rodents, and the like. In embodiments, the nontoxic agricultural formulations can be used to protect plants and crops from environmental stresses like excessive sunlight, freezing or frost conditions, oxidative damage, microbial or fungal growth, osmotic swelling and cracking during wet conditions, and desiccation during low humidity or windy conditions.

After preparation, the agricultural formulations can be delivered to a point of distribution or a point of use. The formulations remain stable for a prolonged period of time, for example, 3-6 months or longer. For application to agricultural targets, the concentrated liquid suspensions can be diluted with a diluent, for example water, and sprayed onto the plant surfaces. In embodiments, the diluted liquid suspension can contain from about 60 to about 99% water. In embodiments, in more detail, the agricultural formulations can be applied onto an agricultural target by spraying, brushing, misting, aerosol application, fogging, backpack spraying, dipping, or irrigation on agricultural targets. The spray solution can further be modified with small amounts of flow aids such as hydrophilic polymers to aid the dispersion of the droplets after spraying and to minimize drift of aerosol to nontarget areas, such as high molecular weight water soluble polyacrylamides. In certain embodiments, the formulations are resistant to friction or rubbing off, and/or they are water-resistant. In other embodiments, water-soluble polymers or waxes such as polyethylene glycols can be added to make the film easily removable after a few washes.

In certain embodiments, the formulation can be applied to an agricultural target, e.g., a plant, a fruit, a vegetable, and the like. For example, in embodiments a formulation can be sprayed onto surfaces of an agricultural target, e.g., fruit or vegetable or plant surfaces (trunks, foliage, leaves, branches, seeds, berries, nuts, roots, and the like) or the soil or other agricultural growth medium, where the formulation can contain active ingredients. Oil droplets containing the active ingredient can coat the agricultural target surface and form a crosslinked film upon drying. In embodiments, the nontoxic barrier coating can protect plants from pests such as weevils, maggots, worms, borers, slugs, flies, fruit flies, moths, grasshoppers, locusts, leafhoppers, leafrollers, aphids, ants, beetles, bugs, thrips, rabbits, deer, rodents, and the like. In embodiments, the nontoxic barrier coating can protect plants and crops from damages caused by diseases transmitted by insects. In embodiments, the nontoxic barrier coating can protect plants from diseases such as fungi, mold, mildew, citrus greening, huanglongbing (HLB) disease, leafspot, brown rot, gall, downy mildew, corn smut, apple rust, leaf curl, leaf spot, mosaic virus, scab, canker, and anthracnose.

In certain embodiments, the drying-oil based agricultural formulation can be used to form a nontoxic barrier coating composition when applied to an agricultural target, e.g., a plant, a fruit, a vegetable, and the like. For example, in embodiments, a formulation can be sprayed onto surfaces of an agricultural target, e.g., fruit or vegetable or plant surfaces (trunks, foliage, leaves, seeds, berries, nuts, roots, branches, and the like), where the formulation can be free of toxic ingredients such as pesticides. In embodiments, the nontoxic barrier coating compositions can deter pest damage due to an altered sensory recognition of the plant surface; for example, the treated plant surface can have a different surface energy, slipperiness, compatibility with insect foot physiological structures, surface texture, odor profile, visual appearance, and heat signature compared with an untreated plant surface. This altered sensory presentation can change the behaviors of insects and animals such that they do not elect to eat or otherwise damage the treated plant. In embodiments, the nontoxic barrier coating compositions can cause the pests to engage in grooming behaviors that can deter them from damaging the agricultural target. In embodiments, the nontoxic barrier coating can immobilize pests that contact the coating by adhering to them. The mechanical and rheological properties of the nontoxic barrier coating can be chosen such that once the coating adheres to the pest, the pest is unable to free itself from the coating, nor is it able to remove the coating from the agricultural target. Such pests may be present on the agricultural target prior to formation of the nontoxic barrier coating, or they may arrive at the agricultural target after the coating has been established. In embodiments, the nontoxic barrier coating composition can serve as protection of the agricultural target from insects, fungi, animals, drought conditions, air pollution damage, heat stress, and solar damage. As used herein, the term "barrier coating" or "barrier coating composition" can be formed as a continuous or discontinuous film or can be otherwise applied at a desired thickness.

In embodiments, the nontoxic barrier coating formulation can be applied to an agricultural target at a dosing rate of about 1 to about 200 lbs (undiluted basis) of formulation per acre of crop. In embodiments, the nontoxic barrier coating formulation can be applied to an agricultural target at a dosing rate of about 3 to about 100 lbs of formulation per acre of crop. In embodiments, the nontoxic barrier coating formulation can be applied to an agricultural target at a dosing rate of about 10 to about 75 lbs of formulation per acre of crop.

Any of these beneficial effects, as described above, are non-limiting examples of desired therapeutic effects. An agricultural treatment is intended to bring about a desired therapeutic effect, i.e., any effect that enhances the production of agricultural products pre-harvest, or that enhances the appearance, taste, durability or other advantageous properties of the agricultural product post-harvest. A material used for an agricultural treatment is an agricultural treatment agent. For example, a desired therapeutic effect can be a protective effect (e.g., protection against pests, fungi, sun damage, drought, ozone, acid rain, environmental toxins, etc.), or a nutrient effect (e.g., delivery of fertilizers, growth hormones, plant nutrients, etc.), or a pre-harvest enhancement effect (e.g., providing an agent that improves the natural properties of the product pre-harvest, including through genetic modification), or a post-harvest protective or enhancement effect (e.g., protecting the skins or surfaces of fruits, vegetables, or seeds post-harvest, or improving their appearance, taste, or commercial attractiveness). Certain fruits and vegetables are subject to crop losses or economic damage due to exposure to environmental stresses like excessive sunlight, freezing or frost conditions, oxidative damage, microbial or fungal growth, osmotic swelling and cracking during wet conditions, and desiccation during low humidity or windy conditions. Reduction of these crop losses and economic damage is another example of a desired therapeutic effect of the coating formulations. Other examples of desired therapeutic effects will be familiar to those having ordinary skill in the art. To achieve a desired therapeutic effect, the target can be treated with the formulation for an exposure time, which is the time deemed appropriate for achieving the desired therapeutic effect. Exposure time for various formulations and targets will be familiar to those of ordinary skill in the art. The exposure time can be preselected, or it can be determined following exposure based on the degree of achievement of the desired therapeutic effect, or based on other parameters that can be observed or determined by the skilled artisan.

In embodiments, the agricultural formulations and methods disclosed herein can prolong the therapeutic effects of an active agricultural ingredient, such as a biological agent or an agricultural chemical. For example, the disclosed formulations can act to protect the active agricultural ingredient from dispersion or deactivation after it contacts the agricultural target. The agricultural formulations disclosed herein can deliver the agricultural chemicals to the agricultural target and retain them there; moreover, the agricultural formulations can protect the agricultural chemicals from adverse conditions such as rainfall, friction, wind, water exposure, and secondary agricultural treatments (e.g., subsequent sprayings or subsequent applications or utilizations of agricultural treatments) that might dilute or remove the agricultural chemical.

In embodiments, the agricultural formulations and methods disclosed herein can be used for delivering biological agents such as beneficial bacteria, beneficial fungi, and/or biological control agents to agricultural targets, and/or retaining biological control agents on agricultural targets. Biological control agents can include a variety of life forms, including plants, insects, and microorganisms such as bacteria, fungi, and viruses. In embodiments, the agricultural formulations can contain biological control agents in amounts from about 0.001% to about 10%. In embodiments, the agricultural formulations can contain biological control agents in amounts from about 0.01% to about 1%. In embodiments, the agricultural formulations can contain biological control agents in amounts from about 0.05% to about 0.5%. In embodiments, the biological control agents comprise at least one strain of *Bacillus thuringiensis* (Bt), or an endotoxin produced by Bt. The use of Bt is understood to be safe and effective for control of insects, and the delivery of Bt by the agricultural formulations and methods disclosed herein can improve or prolong the effectiveness of insect control. Biological control can include the importation of a natural enemy of an agricultural pest, the conservation of a natural enemy of an agricultural pest, or the augmentation of a natural enemy of an agricultural pest. The formulations and methods disclosed herein can serve a role in biological control by delivering biological control agents to an agricultural target in a solid or a liquid formulation, or by providing a barrier coating or film that assists with other biological control endeavors. In embodiments, delivery of the biological control agent by the agricultural formulations and methods disclosed herein can improve or prolong the effectiveness of the biological control agent by improving its rain fastness. In embodiments, for example, a barrier coating as described above can include biological control agents in particulate form, so that the biological control agent is held in proximity to an agricultural surface, and/or it is released in a predetermined, time-release manner.

In embodiments, biological control agents may be formulated in liquid or solid form. For example, commercially available suspensions of spores, toxins, fungi, virus particles, and the like, can be sprayed onto crops like conventional insecticides to act as biological control agents. A non-exhaustive list of exemplary biological control agent formulations is set forth in Table 1:

TABLE 1

Representative Microbial Insecticidal Agents

| Pathogen | Host Range |
|---|---|
| *Bacillus thuringiensis* var. Kurstaki | Lepidopteran larvae |
| *Bacillus thuringiensis* var. Aizawai | Lepidopteran larvae |
| *Bacillus thuringiensis* var. Israelensis | Dipteran larvae |
| *Bacillus thuringiensis* var. Tenebrionis | Coleopteran larvae |
| *Bacillus popillae* | Scarab beetle larvae |
| *Nosema locustae* | Grasshoppers and Crickets |
| *Beauveria bassiana* | Larvae of soil dwelling insects |
| *Hirsutella thompsoni* | Phytophagous mites |
| *Lagenidium giganteum* | Mosquito larvae |
| Nuclear polyhedrosis viruses | Lepidopteran larvae |
| Granulosis virus | Codling moth larvae |
| *Steinernema feltiae* | Soil- and wood-dwelling larvae |
| *Heterorhabditis heliothidis* | Soil-dwelling larvae |

(Table from: https://www.cals.ncsu.edu/course/ent425/text19/biocontrol.html (2003))

The formulations and methods described above for producing agricultural treatments comprising solid or liquid agricultural chemicals can also be applied to agricultural treatment agents comprising biological control agents that have been formulated as solids or liquids.

EXAMPLES

Materials
 Boiled linseed oil, Cargill
 National Standard Bentonite 325, Bentonite Performance Minerals LLC
 Industrial Corn Starch, Casco
 Ecosense 919, DOW
 Raw linseed oil, Cargill
 Glycidyl ether of castor oil, CVC Specialty, Moorestown, N.J.
 Pluronic L121, BASF, Florham Park, N.J.
 Isopar M, ExxonMobil Chemical
 Gum rosin, Sigma Aldrich, St. Louis, Mo.
 Arabica Coffee plants, Amazon.com
 Decyl Glucoside, Dow Chemical Connection
 Linseed oil, Sigma Aldrich, St. Louis, Mo.
 Triethylenetetramine (TETA), Sigma Aldrich, St. Louis, Mo.
 Span 85, Tokyo Chemical Industry (TCI)
 SugaNate 160, Colonial Chemical Co.
 Potassium laurate, Viva Corporation
 Xanthan gum, Cargill
 Geraniol, Sigma Aldrich, St. Louis, Mo.
 d-Limonene, Florida Chemical Co.
 Magnesium stearate, Sigma Aldrich, St. Louis, Mo.
 Microcrystalline cellulose, Sigma Aldrich, St. Louis, Mo.
 Castor oil, Sigma Aldrich, St. Louis, Mo.
 Bentonite, Sigma Aldrich, St. Louis, Mo.
 Titanium dioxide, J. T. Baker, Phillipsburg, N.J.
 Precipitated calcium carbonate, Specialty Minerals Inc., New York, N.Y.
 Other materials described in Examples below

Example 1: Preparation of Linseed Oil/Rosin 1:1 Mixture

Rosin was added to linseed oil at a 1:1 weight ratio. The mixture was mixed and heated above 60° C. for 2 hours to solubilize rosin in linseed oil.

Example 2: Preparation of Linseed Oil/Castor Oil Glycidyl Ether/Triethylenetetramine Linseed oil, castor oil glycidyl ether (GE35-H) and triethylenetetramine (TETA) were mixed at a ratio of 1:1:0.05. The mixture was mixed with a vortexer (VWR Scientific Products, Mini Vortexer 945800) for approximately 10 seconds.

Example 3: Preparation of Linseed Oil/Castor Oil Glycidyl Ether/Magnesium Stearate/triethylenetetramine Linseed oil, castor oil glycidyl ether (GE35-H), magnesium stearate, and triethylenetetramine (TETA) were mixed at a ratio of 1:1:0.75:0.05. The mixture was mixed with a vortexer (VWR Scientific Products, Mini Vortexer 945800) for approximately 10 seconds.

Example 4: Methods of Treating an Agricultural Product

The formulations of Example 5 (below) can be applied to cocoa pods in order to reduce damage to the fruit due to the infestation by the cocoa pod borer (*Conopomorpha cramerella*). The formulations can be applied in the various stages of the pod growth, preferably in the time frame when the fruit skin is green, preferably after 2-4 weeks after the pods start growing on the plant. The application can be performed using a standard spray applicator such as a backpack sprayer. This application method is particularly suitable for pre-harvest coating application on large fruits growing on trees such as cocoa, pineapple, apples, and papaya although other application methods like conventional mechanical sprayers employed in large fields for row crops can also be used. The formulation can reside on the cocoa pod skin for a few weeks at a time, protecting the fruit from cocoa pod borer. The coating is expected be flexible and allow for growth of the fruit and a subsequent second application may be necessary a few weeks prior to harvest. After harvest, the fruits with no edible skins (such as cocoa pods) can be processed without a post-harvest wash. Although other fruits and vegetables with edible skins such as papaya, mango, apples, cherries, tomatoes can require a simple post-harvest wash with a mild soap to remove the coating.

This applied coating is expected to produce a high yield of fruit with unblemished and intact skins with no impact of pest infestation. It is expected that the coated fruits and vegetables would be attractive to consumers and safe for consumption with just the washing steps commonly performed by the consumers of these fruits and vegetables.

Example 5: Formulations for Treatment of Agricultural Targets

Formulations were prepared by blending the ingredients as shown in Tables 2 and 3 below. Each of the formulations was a viscous but free-flowing liquid.

TABLE 2

| Test No. | Boiled linseed oil (%) | Kaolin (%) | Isopar M (%) | Pluronic L121 (%) | Linseed oil (%) | Total (%) | Viscosity (cP) |
|---|---|---|---|---|---|---|---|
| 5.1 | 50.1 | 24.8 | 25.1 | 0.0 | 0.0 | 100.0 | 1050 |
| 5.2 | 45.9 | 31.1 | 23.0 | 0.0 | 0.0 | 100.0 | 1530 |
| 5.3 | 39.2 | 41.2 | 19.6 | 0.0 | 0.0 | 100.0 | 1880 |
| 5.4 | 53.7 | 31.4 | 14.9 | 0.0 | 0.0 | 100.0 | >6600 |
| 5.5 | 52.2 | 30.5 | 14.5 | 2.8 | 0.0 | 100.0 | 2960 |
| 5.6 | 51.0 | 29.8 | 14.2 | 5.0 | 0.0 | 100.0 | 2600 |
| 5.7 | 50.0 | 29.2 | 13.9 | 7.0 | 0.0 | 100.0 | 2500 |
| 5.8 | 36.6 | 21.4 | 10.2 | 5.1 | 26.7 | 100.0 | 5000 |

TABLE 3

| Test No. | Boiled linseed oil (%) | Bentonite (%) | Isopar M (%) | Pluronic L121 (%) | Linseed oil (%) | Total (%) | Viscosity (cP) |
|---|---|---|---|---|---|---|---|
| 5.9 | 50.1 | 24.8 | 25.1 | 0.0 | 0.0 | 100.0 | 1070 |
| 5.10 | 45.9 | 31.1 | 23.0 | 0.0 | 0.0 | 100.0 | 2500 |
| 5.11 | 39.2 | 41.2 | 19.6 | 0.0 | 0.0 | 100.0 | 2530 |
| 5.12 | 53.7 | 31.4 | 14.9 | 0.0 | 0.0 | 100.0 | 3130 |
| 5.13 | 52.2 | 30.5 | 14.5 | 2.8 | 0.0 | 100.0 | 3970 |
| 5.14 | 51.0 | 29.8 | 14.2 | 5.0 | 0.0 | 100.0 | >6600 |
| 5.15 | 50.0 | 29.2 | 13.9 | 7.0 | 0.0 | 100.0 | 5130 |
| 5.16 | 36.6 | 21.4 | 10.2 | 5.1 | 26.7 | 100.0 | 920 |

Example 6: Formulations Containing Different Surfactants

Several aqueous surfactants solutions were prepared for incorporation into a formulation. Each solution was prepared at 20% by adding 2 grams of surfactant to 8 grams of tap water. The list of surfactants tested and their hydrophilic-lipophilic balance (HLB) values are listed in Table 4 below:

TABLE 4

| Surfactant solution No. | Surfactant Name | Surfactant Type | Surfactant HLB |
|---|---|---|---|
| 6.1 | Tergitol 15-s-3 | Secondary alcohol ethoxylate | 8.0 |
| 6.2 | Tergitol 15-s-5 | Secondary alcohol ethoxylate | 10.5 |
| 6.3 | Tergitol 15-s-7 | Secondary alcohol ethoxylate | 12.1 |
| 6.4 | Tergitol 15-s-9 | Secondary alcohol ethoxylate | 13.3 |
| 6.5 | Span 20 | Sorbitan monolaurate | 8.6 |
| 6.6 | Span 80 | Sorbitan monooleate | 4.3 |
| 6.7 | Span 85 | Sorbitan trioleate | 1.8 |
| 6.8 | Tween 20 | Ethoxylated sorbitan laurate | 16.7 |
| 6.9 | Tween 60 | Ethoxylated sorbitan stearate | 14.9 |
| 6.10 | Tween 80 | Ethoxylated sorbitan oleate | 15.0 |
| 6.11 | Tween 85 | Ethoxylated sorbitan trioleate | 11.0 |
| 6.12 | Pluronic L121 | PEG/PPG/PEG block copolymer | 1-7 |

An aliquot of 3.60 grams was taken from each of the 20% surfactant solutions of Table 4 and added to separate vials that each contain 21.60 grams of raw linseed oil. The surfactant solutions were agitated vigorously just before transferring to the linseed oil containing vials. After mixing the surfactant solutions with the raw linseed oil 10.80 grams of bentonite was added to each vial and again agitated vigorously. The final component percentages of each sample vial were 60% raw linseed oil, 30% bentonite, 8% water, and 2% surfactant; these samples are listed in Table 5.

The formulations were left undisturbed for 65 hours and then evaluated for stability by assessing how easily the settled bentonite could be re-dispersed. Each vial was gently inverted to see how much the bentonite had settled at the bottom of the vial and how redispersible the settled bentonite was. Inverted samples were rated with a bentonite packing number between 1 and 5 where 1 means "easy to redisperse" and 5 means "difficult to redisperse". Samples with bentonite that re-dispersed upon inversion by gravity alone were noted. Then each sample was shaken vigorously by hand for about 5 seconds each and again evaluated on whether or not the settled bentonite would re-disperse. The results are listed in Table 5 below.

TABLE 5

| Sample Blend No. | Surfactant | Surfactant HLB | Re-suspendable Upon Inversion? | Re-suspendable Upon Shaking? | Bentonite Packing (1 to 5) |
|---|---|---|---|---|---|
| 6.13 | Tergitol 15-s-3 | 8.0 | No | Yes | 5 |
| 6.14 | Tergitol 15-s-5 | 10.5 | Yes | Yes | 2 |
| 6.15 | Tergitol 15-s-7 | 12.1 | Yes | Yes | 2 |
| 6.16 | Tergitol 15-s-9 | 13.3 | No | Yes | 5 |
| 6.17 | Span 20 | 8.6 | No | Yes | 5 |
| 6.18 | Span 80 | 4.3 | Yes | Yes | 2 |
| 6.19 | Span 85 | 1.8 | Yes | Yes | 1 |
| 6.20 | Tween 20 | 16.7 | No | Yes | 5 |
| 6.21 | Tween 60 | 14.9 | No | Yes | 3 |
| 6.22 | Tween 80 | 15.0 | No | No | 5 |
| 6.23 | Tween 85 | 11.0 | No | No | 3 |
| 6.24 | Pluronic L121 | 1-7 | Yes | Yes | 1 |

Example 7: Formulations with Bentonite or Corn Starch Particle Types

The following formulations were prepared.

Formulation #7a: 30% National Standard 325 bentonite, 70% Raw Linseed Oil. Add 9 g of National Standard 325 bentonite to 21 g of Raw Linseed oil. Mix until homogenous.

Formulation #7b: 30% National Standard 325 bentonite, 10% Ecosense 919, 60% Raw Linseed Oil. Make a 9:1 Raw Linseed Oil: Ecosense 919 by combining 18 g of Raw Linseed Oil (RLO) with 3 g of Ecosense 919 (ES). Mix until homogenous. Add 9 g of National Standard 325 bentonite to 21 g of 9:1 Raw Linseed Oil: Ecosense 919 blend. Mix until homogenous.

Formulation #7c: 30% Industrial Corn Starch, 70% Raw Linseed Oil. Add 9 g of Industrial Corn Starch to 21 g of Raw Linseed oil. Mix until homogenous.

Formulation #7d: 30% Industrial Corn Starch, 10% Ecosense 919, 60% Raw Linseed Oil. Make a 9:1 Raw Linseed Oil: Ecosense 919 by combining 18 g of Raw Linseed Oil (RLO) with 3 g of Ecosense 919. Mix until homogenous Add 9 g of Industrial Corn Starch to 21 g of 9:1 Raw Linseed Oil: Ecosense 919 blend. Mix until homogenous.

The formulated 7a, 7b, 7c, and 7d samples were left undisturbed for 2 hours and then observed for oil split and any other settling observations. Next, the samples were inverted to determine the amount of effort required to resuspend the mixture. Water dispersibility tests were performed on formulations that were resuspendable. To conduct a water dispersibility test, 2 g of concentrate was mixed into 31.3 g of tap water and the samples were vortexed. The observations are documented in Table 6.

TABLE 6

| Formulation No. | Particle type | Fluid phase | Oil Split by volume | Ease of resuspending | Dispersible in water |
|---|---|---|---|---|---|
| 7a | Bentonite | RLO | 9% | Very good | No |
| 7b | Bentonite | RLO/ES | 0% | Good | Yes |
| 7c | Corn starch | RLO | 7% | Very good | No |
| 7d | Corn starch | RLO/ES | 2% | Good | Yes |

Example 8: Formulations with Different Surfactants

The following formulations were prepared:
Formulation #8a: 30% National Standard 325, 70% Raw Linseed Oil. Add 9 g of National Standard 325 to 21 g of Raw Linseed oil. Mix until homogenous.
Formulation #8b: 30% National Standard 325, 5% Pluronic L121, 65% Raw Linseed Oil. Make a 19:1 (Raw Linseed Oil: Pluronic L121) blend by combining 19.95 g of Raw Linseed Oil (RLO) with 1.05 g of Pluronic L121. The Pluronic L121 material is 100% actives with no water. Mix until homogenous. Add 9 g of National Standard 325 bentonite to 21 g of oil/surfactant. Mix until homogenous.
Formulation #8c: 30% National Standard 325, 10% Ecosense 919, 60% Raw Linseed Oil. Make a 9:1 Raw Linseed Oil: Ecosense 919 by combining 18.9 g of Raw Linseed Oil (RLO) with 2.1 g of Ecosense 919. Mix until homogenous Add 9 g of National Standard 325 to 21 g of oil/surfactant. Mix until homogenous. The Ecosense 919 surfactant is 50% actives and 50% water.
Formulation #8d: 30% National Standard 325, 10% Decyl Glucoside, 60% Raw Linseed Oil. Make a 9:1 blend of (Raw Linseed Oil: Decyl Glucoside) by combining 18.9 g of Raw Linseed Oil (RLO) with 2.1 g of Decyl Glucoside. Mix until homogenous Add 9 g of National Standard 325 bentonite to 21 g of oil/surfactant. Mix until homogenous. The Decyl Glucoside surfactant is 50% actives.

These formulations were tested according to the following protocol: Allow samples to remain undisturbed for 24 hours. Next measure oil split and any other settling observations. Afterwards invert and determine the amount of effort required to resuspend the mixture. Following these steps, water dispersibility tests were performed on formulations that were resuspendable; 2 g of concentrate were mixed into 31.3 g of tap water and samples were vortexed. Results of testing are documented in Table 7.

TABLE 7

| Sample No. | Surfactant | Oil Split | Ease of resuspending | Water dispersibility |
|---|---|---|---|---|
| 8a | None | 72% | Good | Poor |
| 8b | Ecosense 919 (10%) | 2% | Poor | Good |
| 8c | Decyl glucoside (10%) | 6% | Poor | Good |
| 8d | Pluronic L121 (5%) | 32% | Fair | Poor |

Example 9: Formulations with Suspension Additives

The following formulations were prepared:
Formulation #9a: 30% National Standard 325, 10% Pluronic L121, 60% Raw Linseed Oil. Combine 18 g of Raw Linseed Oil (RLO) with 3 g of Pluronic L121. Mix until homogenous. Add 9 g of National Standard 325 to 21 g of oil/surfactant. Mix until homogenous.
Formulation #9b: 30% National Standard 325, 10% Pluronic L121, 3% Magnesium Stearate, 57% Raw Linseed Oil. Combine 17.1 g of Raw Linseed Oil (RLO) with 3 g of Pluronic L121. Mix until homogenous. Next add 0.9 g of Magnesium Stearate. Add 9 g of National Standard 325 to 21 g of oil/surfactant. Mix until homogenous.
Formulation #9c: 30% National Standard 325, 10% Pluronic L121, 3% Microcrystalline Cellulose (MCC), 57% Raw Linseed Oil. Combine 17.1 g of Raw Linseed Oil (RLO) with 3 g of Pluronic L121. Mix until homogenous. Next add 0.9 g of MCC. Add 9 g of National Standard 325 bentonite to 21 g of oil/surfactant. Mix until homogenous.

These formulations were tested according to the following protocol: Samples were left undisturbed for 24 hours. Next measure oil split and any other settling observations. Afterwards invert and determine the amount of effort required to resuspend the mixture. At the conclusion of these tests, the following results were observed: The magnesium stearate containing sample (#9b) had increased viscosity compared with sample #9a and there was no oil split layer. The control sample 9a had an oil split layer. The MCC-containing sample (#9c) displayed less of an oil split and was easier to resuspend than the control sample 9a.

Example 10: Agricultural Formulation with Insecticidal Soap

A formulation suitable for agricultural application was prepared with the insecticidal soap potassium laurate. An 18.88 g aliquot of raw linseed oil was added to a 40 mL glass vial, followed by 1.60 g of SugaNate 160 and 1.60 g of a 40% Span 85 dispersion in water. These substances were shaken and vortexed together. Next, a 0.32 g sample of potassium laurate was added to the vial and again shaken and vortexed. A 0.32 g sample of xanthan gum followed and the sample was shaken and vortexed once more. The last addition to the concentrated form was a 9.60 g sample of bentonite that was added in thirds, with shaking and vortexing taking place between each addition. After all of the bentonite was added, the vial was placed on a bottle roller for 30 minutes to disperse any remaining solid clumps. The finished product was a formulation suitable for agricultural application containing the insecticidal soap. To prepare a solution for application to plants, a 1.0 g aliquot of the formulation was taken and added to a 20 mL vial containing 15.65 g of tap water. The vial was shaken and vortexed and observed. After 1 to 2 minutes the vial showed a stable dispersion in water without any sign of solids settling or oil splitting for at least 30 minutes.

Example 11: Agricultural Formulation with Geraniol

A formulation suitable for agricultural application was prepared with geraniol, an essential oil that is an insect repellent. An 18.24 g aliquot of raw linseed oil was added to a 40 mL glass vial, followed by 1.60 g of SugaNate 160 and 1.60 g of a 40% Span 85 dispersion in water. These substances were shaken and vortexed together to ensure a well-mixed product. A 0.64 g sample of geraniol was added to the vial and again shaken and vortexed. A 0.32 g sample of xanthan gum followed and the sample once more shaken and vortexed. The last addition to the formulation was a 9.60 g sample of bentonite that was added in thirds, with shaking and vortexing taking place between each addition. After all of the bentonite was added the vial was placed on a bottle roller for 30 minutes to disperse any remaining solid clumps. The finished product was a formulation suitable for agricultural application containing an insect repellent essential oil. To prepare a dilution for application on plants, a 1.0 g aliquot of the formulation was taken and added to a 20 mL vial containing 15.65 g of tap water. The vial was shaken and vortexed and observed. After 30 minutes the emulsion was showing no signs of bentonite settling or oil separation.

Example 12: Agricultural Formulation with d-Limonene

A formulation suitable for agricultural application was prepared with d-Limonene, a botanical oil insecticide. An 18.24 g aliquot of raw linseed oil was added to a 40 mL glass vial, followed by 1.60 g of SugaNate 160 and 1.60 g of a 40% Span 85 dispersion in water. These substances were shaken and vortexed together to ensure a well-mixed product. A 0.64 g sample of d-Limonene was added to the vial and again shaken and vortexed. A 0.32 g sample of xanthan gum followed and the sample once more shaken and vortexed. The last addition to the concentrated form was a 9.60 g sample of bentonite that was added in thirds, with shaking and vortexing taking place between each addition. After all of the bentonite was added the vial was placed on a bottle roller for 30 minutes to disperse any remaining solid clumps. The finished product was a formulation suitable for agricultural application containing d-limonene. To prepare a dilution for application on plants, a 1.0 g aliquot of the mixture was taken and added to a 20 mL vial containing 15.65 g of tap water. The 20 mL vial was shaken and vortexed and observed. After 30 minutes the emulsion was showing no signs of bentonite settling or oil separation.

Example 13: Agricultural Formulation with Capsaicin

A formulation suitable for agricultural application was prepared with the biopesticide capsaicin. An 18.24 g aliquot of raw linseed oil was added to a 40 mL glass vial, followed by 1.60 g of SugaNate 160 and 1.60 g of a 40% Span 85 dispersion in water. These substances were shaken and vortexed together to ensure a well-mixed product. A 0.64 g sample of Tobasco Chipotle Pepper Sauce with 1500-2500 heat units on the Scoville scale (McIlhenny Company) was added to the vial followed by more shaking and vortexing. The amount of capsaicin in the sauce was about 90-160 ppm based on conversion of the Scoville unit scale where 16 million Scoville units is equal to pure capsaicin. A 0.32 g sample of xanthan gum followed and the sample was once more shaken and vortexed. The last addition to the concentrated form was a 9.60 g sample of bentonite that was added in thirds, with shaking and vortexing taking place between each addition. After all of the bentonite was added the vial was placed on a bottle roller for 30 minutes to disperse any remaining solid clumps. The finished product was a formulation suitable for agricultural application containing capsaicin. To prepare a dilution for application on plants, a 1.0 g aliquot of the mixture was taken and added to a 20 mL vial containing 15.65 g of tap water. The 20 mL vial was shaken and vortexed and observed. After 30 minutes the emulsion was showing no signs of bentonite settling or oil separation.

Example 14: Agricultural Formulation with Neem Oil

A formulation suitable for agricultural application was prepared with neem oil, a vegetable oil used as a pesticide for organic farming. A 15.68 g aliquot of raw linseed oil was added to a 40 mL glass vial, followed by 1.60 g of SugaNate 160 and 1.60 g of a 40% Span 85 dispersion in water. These substances were shaken and vortexed together to ensure a well-mixed product. A 3.20 g sample of neem oil (Blue Lily Organics) was added to the vial and again shaken and vortexed. A 0.32 g sample of xanthan gum followed and the sample was once more shaken and vortexed. The last addition to the concentrated form was a 9.60 g sample of bentonite that was added in thirds, with shaking and vortexing taking place between each addition. After all of the bentonite was added the vial was placed on a bottle roller for 30 minutes to disperse any remaining solid clumps. The finished product was a formulation suitable for agricultural application containing neem oil. To prepare a dilution for application on plants, a 1.0 g aliquot of the mixture was taken and added to a 20 mL vial containing 15.65 g of tap water. The 20 mL vial was shaken and vortexed and observed. After 30 minutes the emulsion was showing no signs of bentonite settling or oil separation.

Example 15: Rainfastness of Agricultural Formulation Containing Neem Oil

The rainfastness of the agricultural formulation of Example 14 was tested as follows. A comparative neem oil formulation was prepared with: 15.90 g of tap water was added to a 20 mL vial, followed by 1.0 g of neem oil, 0.0175 g of potassium laurate, and 0.1134 g of 1.0M sodium hydroxide (Sigma Aldrich). This comparative mixture was vortexed and found to be stable enough to spray. 3 g of the comparative neem oil formulation was sprayed onto the surface of a tared 5"×3" acrylic sheet (Plaskolite brand) and then rolled with a paint roller. The acrylic sheet material was used as a model of the plant surface. On a separate tared 5"×3" acrylic sheet, a 3.0 g aliquot of the diluted agricultural formulation of Example 14 with neem oil was sprayed and rolled with a paint roller. Both treated acrylic sheets were allowed to dry for 18 hours so the coating could cure, their weights were recorded, and then the sheets were sprayed with water from a spray bottle for 15 seconds to simulate rainfall. After being sprayed with water, both sheets were put in a forced convection air oven at 37 C for 1.5 hours to dry, and their weights were recorded again. The sheet that was treated with the agricultural formulation of Example 14 containing neem oil retained 68% of the applied coating after simulated rainfall, while the sheet that was treated with the comparative formulation of neem oil, potassium laurate, and sodium hydroxide did not retain any of the coating after a simulated rainfall.

Example 16: Agricultural Formulation with Camphor Oil

A formulation suitable for agricultural application was prepared with white camphor oil, an essential oil used as a pest repellent. A 15.68 g aliquot of raw linseed oil was added to a 40 mL glass vial, followed by 1.60 g of SugaNate 160 and 1.60 g of a 40% Span 85 dispersion in water. These substances were shaken and vortexed together to ensure a well-mixed product. A 3.20 g sample of white camphor oil (Sigma Aldrich) was added to the vial and again shaken and vortexed. A 0.32 g sample of xanthan gum followed and the sample was once more shaken and vortexed. The last addition to the concentrated form was a 9.60 g sample of bentonite that was added in thirds, with shaking and vortexing taking place between each addition. After all of the bentonite was added the vial was placed on a bottle roller for 30 minutes to disperse any remaining solid clumps. The finished product was a formulation suitable for agricultural application containing white camphor oil. To prepare a dilution for application on plants, a 1.0 g aliquot of the mixture was taken and added to a 20 mL vial containing 15.65 g of tap water. The 20 mL vial was shaken and vortexed and observed. After 30 minutes the emulsion was showing no signs of bentonite settling or oil separation.

Example 17: Agricultural Formulation with Beneficial Fungi

A formulation suitable for agricultural application was prepared with beneficial fungi. An 18.56 g aliquot of raw linseed oil was added to a 40 mL glass vial, followed by a 1.60 g aliquot of the product SugaNate 160 and a 1.60 g aliquot of a 40% Span 85 dispersion in water. These substances were shaken and vortexed together to ensure a well-mixed product. A 0.32 g sample of the product "White Shark" (Plant Revolution Inc.) was added to the vial and again shaken and vortexed. White Shark is a beneficial fungus powder containing 187,875 CFU/g of *Trichoderma koningii* and 125,250 CFU/g of *Trichoderma harzianum*. A 0.32 g sample of xanthan gum was then added, and the mixture was once more shaken and vortexed. A 9.60 g sample of bentonite was then added in thirds, with shaking and vortexing taking place between each addition. After all of the bentonite was added, the vial was placed on a bottle roller for 30 minutes to disperse any remaining solid clumps. The finished product was a formulation suitable for agricultural application containing beneficial fungi. To prepare a dilution for application on plants, a 1.0 g aliquot of the mixture was taken and added to a 20 mL vial containing 15.65 g of tap water. The 20 mL vial was shaken and vortexed and observed. After 30 minutes the emulsion was showing no signs of bentonite or fungal spore powder settling or oil separation.

Example 18: Agricultural Formulation with Sulfur

A formulation suitable for agricultural application was prepared with elemental sulfur, which can be used as a fungicide. An 18.56 g aliquot of raw linseed oil was added to a 40 mL glass vial, followed by 1.60 g of SugaNate 160 and 1.60 g of a 40% Span 85 dispersion in water. These substances were shaken and vortexed together to ensure a well-mixed product. A 0.32 g sample of elemental sulfur powder was added to the vial and again shaken and vortexed. A 0.32 g sample of xanthan gum was then added, and the mixture was once more shaken and vortexed. A 9.60 g sample of bentonite was then added in thirds, with shaking and vortexing taking place between each addition. After all of the bentonite was added the vial was placed on a bottle roller for 30 minutes to disperse any remaining solid clumps. The finished product was a formulation suitable for agricultural application containing beneficial fungi. To prepare a dilution for application on plants, a 1.0 g aliquot of the mixture was taken and added to a 20 mL vial containing 15.65 g of tap water. The 20 mL vial was shaken and vortexed and observed. After 30 minutes the emulsion was showing no signs of bentonite settling or oil separation.

Example 19: Rainfastness of Agricultural Formulation with Geraniol

The rainfastness of the agricultural formulation of Example 11 was tested as follows. A comparative geraniol formulation was prepared with: 15.90 g of tap water was added to a 20 mL vial, followed by 1.0 g of geraniol, 0.0175 g of potassium laurate, and 0.1134 g of 1.0M sodium hydroxide (Sigma Aldrich). This comparative mixture was vortexed and found to be stable enough to spray. 3 g of the comparative geraniol formulation was sprayed onto the surface of a tared 5"×3" acrylic sheet (Plaskolite brand) and then rolled with a paint roller. On a separate tared 5"×3" acrylic sheet, a 3.0 g aliquot of the diluted agricultural formulation of Example 11 with geraniol was sprayed and rolled with a paint roller. Both treated acrylic sheets were allowed to dry for 18 hours so the coating could cure, their weights were recorded, and then the sheets were sprayed with water from a spray bottle for 15 seconds to simulate rainfall. After being sprayed with water, both sheets were put in a forced convection air oven at 37 C for 1.5 hours to dry, and their weights were recorded again. The sheet that was treated with the agricultural formulation of Example 11 containing geraniol retained 34.5% of the applied coating after simulated rainfall, while the sheet that was treated with the comparative formulation of geraniol, potassium laurate, and sodium hydroxide did not retain any of the coating after a simulated rainfall.

Example 20: Rainfastness of Agricultural Formulation with d-Limonene

The rainfastness of the agricultural formulation of Example 12 was tested as follows. A comparative d-limonene formulation was prepared with: 15.90 g of tap water was added to a 20 mL vial, followed by 1.0 g of d-limonene, 0.0175 g of potassium laurate, and 0.1134 g of 1.0M sodium hydroxide (Sigma Aldrich). This comparative mixture was vortexed and found to be stable enough to spray. 3 g of the comparative d-limonene formulation was sprayed onto the surface of a tared 5"×3" acrylic sheet (Plaskolite brand) and then rolled with a paint roller. On a separate tared 5"×3" acrylic sheet, a 3.0 g aliquot of the diluted agricultural formulation of Example 12 with d-limonene was sprayed and rolled with a paint roller. Both treated acrylic sheets were allowed to dry for 18 hours so the coating could cure, their weights were recorded, and then the sheets were sprayed with water from a spray bottle for 15 seconds to simulate rainfall. After being sprayed with water, both sheets were put in a forced convection air oven at 37° C. for 1.5 hours to dry, and their weights were recorded again. The sheet that was treated with the agricultural formulation of Example 12 containing d-limonene retained 53.9% of the applied coating after simulated rainfall, while the sheet that was treated with the comparative formulation of d-limonene, potassium laurate, and sodium hydroxide did not retain any of the coating after a simulated rainfall.

Example 21: Agricultural Formulation

A formulation suitable for agricultural application was prepared as follows. An 18.88 g aliquot of raw linseed oil was added to a 40 mL glass vial, followed by 1.60 g of SugaNate 160 and 1.60 g of a 40% Span 85 dispersion in water. These substances were shaken and vortexed together. A 0.32 g sample of xanthan gum was then added, and the mixture was once more shaken and vortexed. A 9.60 g sample of bentonite was then added in thirds, with shaking and vortexing taking place between each addition. After all of the bentonite was added the vial was placed on a bottle roller for 30 minutes to disperse any remaining solid clumps. The finished product was a formulation suitable for agricultural application in the form of a fluid suspension. To prepare a dilution for application on plants, a 1.0 g aliquot of the mixture was taken and added to a 20 mL vial containing 15.65 g of tap water. The 20 mL vial was shaken and vortexed and observed. After 30 minutes the emulsion was showing no signs of solids settling or oil splitting.

Example 22: Rain Fastness of Agricultural Formulation with *Trichoderma*

The rain fastness of the agricultural formulation of Example 17 was tested as follows. A comparative *Trichoderma* formulation (Example 22a) was prepared with: 14.85 g of tap water was added to a 20 mL vial, followed by 0.15 g of the product "White Shark" (Plant Revolution Inc.). This comparative mixture was vortexed and found to be stable enough to spray. 3 g of this comparative *Trichoderma* formulation was then sprayed onto the surface of a 5"×3" acrylic sheet (Plaskolite brand). On two separate 5"×3" acrylic sheets, 3 g of diluted agricultural formulation of Example 17 (samples a and b) with *Trichoderma* was sprayed onto each surface. All of the treated acrylic sheets were placed in a convection-free oven at 37° C. for 1.5 hours to dry. Optical images of each sheet were taken using an optical microscope (Zeiss AxioImager.A1M). Each sheet was then exposed to simulated rainfall by spraying water from a spray bottle for 15 seconds. After being sprayed with water, the sheets were placed in a convection-free oven at 37° C. for 1.5 hours to dry. Images of each sheet were again taken using an optical microscope. ImageJ software (National Institutes of Health) was used to analyze the particle distribution in each acrylic sheet, and these results are summarized in Table 8. The sheets that were treated with the diluted agricultural formulation of Example 17 containing *Trichoderma* retained 81-86% of the applied particles after simulated rainfall, while the sheet that was treated with comparative formulation of *Trichoderma* retained only 8% of the applied particles after simulated rainfall.

TABLE 8

| | Before Simulated Rainfall | | After Simulated Rainfall | | |
|---|---|---|---|---|---|
| Sample Source | Avg. Particle Diameter [μm] | Particle Density [$mm^{-2}$] | Avg. Particle Diameter [μm] | Particle Density [$mm^{-2}$] | % Removed by Rainfall |
| Example 22a | 3.2 | 1200 | 2.5 | 92 | 92 |
| Example 17 (sample a) | 4.1 | 6800 | 3.4 | 5500 | 19 |
| Example 17 (sample b) | 5.0 | 5900 | 3.5 | 5100 | 14 |

Example 23: Agricultural Formulations

Several surfactant products were evaluated by incorporating each one into an agricultural formulation sample. 8 formulation samples were prepared, using the ingredients listed in Table 9 below:

TABLE 9

| Sample | Surfactant/Source (% actives) | Raw Linseed Oil (gms) | Amount Surfactant (gms) |
|---|---|---|---|
| 23.1 | Lecisoy 400/Cargill (100%) | 19.84 | 0.64 |
| 23.2 | Topcithin UB/Cargill (100%) | 19.84 | 0.64 |
| 23.3 | Triton BG-10/DOW (70%) | 19.57 | 0.91 |
| 23.4 | Triton CG-110/DOW (50%) | 19.20 | 1.28 |
| 23.5 | Triton H-55/DOW (50%) | 19.20 | 1.28 |

TABLE 9-continued

| Sample | Surfactant/Source (% actives) | Raw Linseed Oil (gms) | Amount Surfactant (gms) |
|---|---|---|---|
| 23.6 | Witconate AOS/Akzo Nobel (40%) | 18.88 | 1.60 |
| 23.7 | Witconate NAS-8/Akzo Nobel (40%) | 18.88 | 1.60 |
| 23.8 | Tergitol 15-s-5/Sigma (100%) | 19.84 | 0.64 |

To prepare the samples, eight 40 mL vials were first filled with raw linseed oil (Cargill) in the amounts listed in Table 9. After the linseed oil was added, an aliquot of each surfactant product was added to the corresponding 40 mL vial as listed in Table 9, in an amount that was calculated so that 2% of the active surfactant ingredient would be present in the final sample formulation. A dispersion of 40% Span 85 (Millipore) was then vigorously shaken and then added in 1.60 gram amounts to each individual vial. Each sample vial was then shaken and vortexed together to ensure a well-mixed product. Following this, 0.32 grams of xanthan gum was added to each vial, and each vial was shaken and vortexed. The last addition to each vial was a 9.60 gram sample of bentonite that was added in thirds, with shaking and vortexing taking place in between each addition. After all of the bentonite had been added, each vial was placed on a roller for 30 minutes to disperse any remaining solid clumps. After 30 minutes, each vial was removed and a 1.0 gram aliquot of each mixture was taken and added to a 20 mL vial containing 15.65 grams of tap water, forming diluted samples. The diluted samples were shaken and vortexed vigorously and observed. The concentrated samples were left to sit overnight.

A control was then prepared in the same manner using the amounts of 18.72 grams raw linseed oil, 1.60 grams 40% Span 85 dispersion in water, 1.60 grams water, 0.48 grams xanthan gum, and 9.60 grams bentonite. After 30 minutes on the roller a 1.0 gram aliquot was taken and added to a 20 mL vial containing 15.65 grams of tap water, to form a diluted sample. The diluted sample was shaken and vortexed vigorously and observed. The concentrated sample was left to sit overnight.

The diluted samples were evaluated as to whether the bentonite remained dispersed or settled out, and as to whether the oil remained dispersed throughout the sample or became separated at the top. A good result was an even dispersion of clay and oil throughout the water. The results are listed in Table 10 below:

TABLE 10

| Sample | Surfactant | Bentonite dispersed or settled | Oil dispersed or separated |
|---|---|---|---|
| 23.1 | Lecisoy 400 | Settled | Dispersed |
| 23.2 | Topcithin UB | Settled | Dispersed |
| 23.3 | Triton BG-10 | Dispersed | Dispersed |
| 23.4 | Triton CG-110 | Dispersed | Dispersed |
| 23.5 | Triton H-55 | Settled | Dispersed |
| 23.6 | Witconate AOS | Dispersed | Dispersed |
| 23.7 | Witconate NAS-8 | Partially settled | Dispersed |
| 23.8 | Tergitol 15-S-5 | Settled | Dispersed |
| 23.9 | None (Control) | Settled | Separated |

The concentrated formulations were left untouched for 71 hours and then evaluated for stability by assessing how easily the settled bentonite was able to redisperse. Each vial was gently inverted to see how compacted the bentonite at the bottom had become and how redispersible the bentonite was. Inverted samples were graded with a "Dispersibility" number between 1 and 5 where 1 means "readily dispersible" and 5 means "not dispersible". Samples with bentonite that redispersed by simple inversion alone were noted. Then each sample was shaken vigorously by hand for about 5 seconds each and again evaluated on whether or not the settled bentonite would redisperse. The results are listed in Table 11 below:

TABLE 11

| Sample | Surfactant | Resuspendable Upon Inversion? | Resuspendable Upon Shaking? | Bentonite dispersibility (1 to 5) |
|---|---|---|---|---|
| 23.1 | Lecisoy 400 | No | Yes | 2 |
| 23.2 | Topcithin UB | No | Yes | 2 |
| 23.3 | Triton BG-10 | No | Yes | 2 |
| 23.4 | Triton CG-110 | No | Yes | 2 |
| 23.5 | Triton H-55 | No | Yes | 3 |
| 23.6 | Witconate AOS | No | No | 5 |
| 23.7 | Witconate NAS-8 | No | Yes | 4 |
| 23.9 | Tergitol 15-S-5 | Yes | Yes | 1 |
| 23.9 | None (Control) | No | Yes | 1 |

Example 24: Seed Coating with Agricultural Formulations

Burpee Pea Super Snappy seeds were coated with aqueous mixtures of 3%, 10%, and 16% (w/w) of the agricultural formulation of Example 21 in water; the coated seeds were then air dried at 22° C. The seeds (six replicates of each coating type) were planted in Conrad Fafard Organic Potting Mix and watered daily. Germination rates, as determined by % of the planted seeds that sprouted, were recorded after different amounts of time as shown in Table 12.

TABLE 12

| | Germination Rates | | | |
|---|---|---|---|---|
| Days after planting | Control (no coating) | 3% Coating | 10% Coating | 16% Coating |
| 3 | 0% | 67% | 67% | 33% |
| 4 | 17% | 83% | 67% | 50% |
| 5 | 50% | 100% | 67% | 50% |
| 6 | 50% | 100% | 67% | 50% |
| 7 | 50% | 100% | 67% | 67% |
| 10 | 50% | 100% | 67% | 67% |
| 11 | 50% | 100% | 67% | 67% |
| 12 | 50% | 100% | 67% | 67% |

Example 25: Agricultural Formulations with Stabilizers

Several different additives were evaluated for their ability to stabilize the formulation when it was diluted with water. To prepare these formulations, 14 separate vials were each filled with 18.88 grams of raw linseed oil (Cargill) followed by a 1.60 gram aliquot of the product SugaNate 160 (Colonial Chemical Company) and a 1.60 gram aliquot of a 40% Span 85 (Millipore) dispersion in water. These substances were shaken and vortexed together to ensure a well-mixed product. A single 0.32 gram sample of each emulsion stabilizer (as listed in Table 13) was measured out and added to each vial. After each vial received its respective emulsion stabilizer, the samples were again shaken and vortexed. Then, 9.60 grams of bentonite was added in thirds, with shaking and vortexing taking place in between each addition. After all of the bentonite was added to a vial, it was placed on a roller for 30 minutes to disperse any remaining solid clumps. After 30 minutes, each vial was removed and a 1.0 gram aliquot of each mixture was taken and added respectively to a 20 mL vial containing 15.65 grams of tap water, to form a dilute sample. The dilute samples were shaken and vortexed vigorously and observed.

The dilute samples were evaluated as to whether the bentonite remained dispersed or settled out, and as to whether the oil remained dispersed throughout the sample or became separated at the top. A good result was an even dispersion of clay and oil throughout the water. The results are listed in Table 13 below:

TABLE 13

| Test # | Emulsion Stabilizer (Source) | Bentonite Behavior | Oil Behavior |
|---|---|---|---|
| 25.1 | Alginic acid (Sigma) | Settles quickly | Separates |
| 25.2 | Carrageenan (Sigma) | Settles quickly | Dispersed |
| 25.3 | CMC Na+ MW = 700,000 (Sigma) | Dispersed | Dispersed |
| 25.4 | Gelatin (Sigma) | Settles quickly | Separates |
| 25.5 | Pectin (CP Kelco) | Settles quickly | Separates |
| 25.6 | Pearl starch (Sigma) | Settles quickly | Separates |
| 25.7 | Gum Guar Carboxymethyl ether 2-hydroxypropyl ether, sodium salt (Sigma) | Settles slowly | Dispersed |
| 25.8 | Hydroxy propyl cellulose Mn = 10,000 (Sigma) | Settles, not fully dispersed | Dispersed |
| 25.9 | Hydroxy propyl cellulose Mn = 100,000 (Sigma) | Settles, not fully dispersed | Dispersed |
| 25.10 | Ethyl cellulose 4,000 cP (Sigma) | Some settling, partially dispersed | Separates |
| 25.11 | Ethyl cellulose 100,000 cP (Sigma) | Some settling, partially dispersed | Separates |
| 25.12 | Hydroxypropyl methyl cellulose (Sigma) | Settles slowly | Separates |
| 25.13 | CMC Na+ MW~250,000 (Sigma) | Settles | Separates |
| 25.14 | None (control) | Settles quickly | Separates |

Example 26: *Trichoderma* Spore Germination in Agricultural Formulations

The agricultural formulation of Example 17 was compared to a control formulation to assess the viability of the *Trichoderma* spores that each contained. The control *Trichoderma* formulation was prepared as follows: 0.15 gm of the *Trichoderma*-containing product "White Shark" was added to 14.85 g of tap water in a 20 mL vial. This control mixture was vortexed and found to be stable enough to spray. 1 g of this control *Trichoderma* formulation was then sprayed onto the surface of a 1"×3" glass slide. On a separate 1"×3" glass slide, 1 g of the diluted agricultural formulation of Example 17 was sprayed on the surface. Both treated glass slides were then placed in a convection-free oven at 37 C for 1.5 hours to dry. After this drying had taken place, a 0.2 g aliquot of a 0.02% aqueous potato dextrose agar ("PDA", Sigma Aldrich) solution was pipetted onto each previously coated glass slide. Each glass slide was then placed on top of separate 200 mL containers, each of which was then affixed with an adhesive inside separate 1 L containers. 60 g of tap water was placed inside each 1 L container to create a high humidity environment for the *Trichoderma* spores to proliferate, and to decrease evaporation rate of PDA media. Both prepared 1 L containers were sealed with a cap and incubated in a convection-free oven at 25° C. for 3 days. After 3 days, the slides were removed from oven and inspected for *Trichoderma* spore germination via colony formation using a Zeiss AxioImager.A1M microscope. Both the control *Trichoderma* formulation and the formulation of Example 17 showed signs of *Trichoderma* germination as evidenced by the appearance of branched hyphae.

Example 27: *Trichoderma* Spore Germination in Agricultural Formulations After Simulated Rainfall The experiment of Example 26 was reproduced in order to test the control and the experimental sample for the presence of viable spores following exposure to simulated rainfall. A control *Trichoderma* formulation was prepared as described in Example 26. A test formulation was prepared as described in Example 17. Each formulation was applied to a glass slide and dried as described in Example 26. After this drying had taken place, each glass slide was then exposed to simulated rainfall by spraying water from a spray bottle for 15 seconds. After spraying with water, both slides were placed in a convection-free oven at 37° C. for 1.5 hours to dry.

After drying, each slide received a 0.2 g aliquot of a 0.02% aqueous potato dextrose agar solution and was incubated as described in Example 26. After 3 days, samples were inspected for spore germination as described in Example 26. The glass slide that was treated with agricultural formulation of Example 17 containing *Trichoderma* showed germination (as evidenced by the appearance of branched hyphae) even after simulated rainfall, while the glass slide that was treated with the comparative formulation of *Trichoderma* did not exhibit any germination of *Trichoderma* after simulated rainfall.

Example 28-32 Materials

The following materials were used for Examples 28-32, in addition to the materials described earlier:
 Raw linseed oil (RLO), (CAS#67746-08-1) (Cargill)
 Bentonite (Sodium bentonite clay) (CAS#1302-78-9) (BPM/Halliburton)
 Jarfactant 325N, an alkylpolyglycoside surfactant with an alkyl chain length of 9-11 carbon units (CAS#132778-08-6) (Jarchem)
 Span 85 (sorbitan trioleate) (CAS#26266-58-0)
 PLURONIC® F108 (PEG-PPG-PEG triblock copolymer and surfactant) (CAS#9003-11-6) (Sigma-Millipore)
 Water (tap water from Cambridge Mass.) (all water is tap unless specified)
 Ammonium hydroxide: a 30% solution of ammonia and water (CAS#1336-21-6)
 DOWANOL™ TPM (Tripropylene Glycol Methyl Ether) (Dow Chemicals)
 THIXCIN® R (non-hygroscopic castor oil derivative) (Elementis Specialties)
 Break Thru SP133 (additive based on based on polyglycerol esters and fatty acid esters) (Evonik)
 HPMC—hydroxypropylmethyl cellulose (Methocel E15 LV, CAS#9004-54-3) (Dow Chemical Company)

Example 28: Formulation Preparation

An agricultural formulation was prepared as a concentrate, in large and small batch sizes (small ≤250 g), using the reagents in amounts set forth below in Table 14:

TABLE 14

| Component | wt % | Small batch wt (g) | Large batch wt (g) |
|---|---|---|---|
| RLO | 54.7 | 43.76 | 2461.50 |
| Jarfactant 325N | 2.0 | 1.60 | 90.00 |
| Span 85 | 2.0 | 1.60 | 90.00 |
| Water | 2.27 | 1.81 | 102.00 |
| Bentonite | 38.2 | 30.56 | 1719.00 |
| Pluronic F108 | 0.5 | 0.40 | 22.50 |
| Ammonium hydroxide | 0.333 | 0.27 | 15.00 |
| TOTAL | 100 | 80.00 | 4500.00 |

To prepare the above formulations, a polymer solution was first prepared. An appropriate amount of PLURONIC® F108 was weighed, in accordance with the amount designated in Table 14. An appropriate amount of water was added to a mixing vessel (e.g., a beaker for a large solution or a centrifuge tube for a small solution) so that an 18.2% solution of the PLURONIC® F108 could be made. The PLURONIC® F108 was then added gradually and mixed into the water, with care being taken that the PLURONIC® F108 was mobilized thoroughly into the water and did not adhere to the vessel walls. When a centrifuge tube mixing vessel was used, it was then capped and placed on a laboratory roller at about 70% full speed. When a beaker-sized mixing vessel was used, it was mixed with a laboratory mixer using the fan blade mixing shaft of appropriate size for the mixing vessel. The PLURONIC® F108 was mixed into the water until there was no solid polymer left, only water and foam. When clumps started to form, additional agitation and separation with a spatula was used to ensure complete dissolution. After it was verified that there was no longer any solid polymer (usually after several hours of mixing), the mixing vessel was removed from the mixing apparatus and was allowed to sit undisturbed for a period of time, allowing the foam above the solution to relax back into full liquid form; this resting phase required several hours, sometimes overnight.

After preparing the PLURONIC® F108 solution, an appropriate amount of bentonite was weighed into a designated solids container. The solids container was then shaken to break up any solids clumps. Appropriate amounts of RLO, PLURONIC® F108 solution, and Jarfactant 325N were then combined, and an appropriate amount of the NaOH solution was added. These liquids were mixed briefly using an overhead mixer with a fan shaft blade until homogeneous. After the RLO and aqueous reagents were combined, an appropriate amount of Span 85 was added to the stirring sample. All liquid reagents were mixed thoroughly before that mixture was combined with the solids. The solid material was added gradually and mixed thoroughly during the addition process.

Example 29: Sedimentation Stability

Sedimentation stability was tested for the formulation prepared according to Example 28. To do so, a transparent plastic cylinder 1" in diameter was filled with a 12" column of freshly prepared formulation. Sedimentation of the aqueous phase in the concentrate resulted in the appearance of a layer of clear fluid at the top of the column, and the creation of a dense concentrate at the bottom of the column. The thickness of the clear fluid layer was determined by eye. The thickness of the dense concentrate was determined either by pouring the fluid from the tube and noting the height of the column of non-pourable material that remained behind, or by lowering a weight into the column and noting the depth at which the weight ceased to penetrate the fluid. Sedimentation measurements were made periodically until the sum of the clear and dense layers reached approximately 100%; see Table 15 below.

TABLE 15

Clear and dense layer thicknesses (as percentage of original formulation height) over time

| Time [days] | % clear | % dense |
|---|---|---|
| 0.0 | 0% | 0% |
| 3.7 | 4% | |
| 4.7 | 5% | |
| 5.7 | 7% | |
| 6.7 | 9% | 34% |
| 9.8 | 12% | |
| 10.7 | 13% | |
| 13.0 | 14% | |
| 13.9 | 13% | 75% |
| 16.7 | 15% | |
| 20.1 | 15% | |
| 20.8 | 16% | 86% |

Example 30: Stabilizing the formulation Against Sedimentation with DOWANOL™ TPM

The agricultural formulation prepared according to Example 28 was used for the following experiment. 200 g of the agricultural formulation was added to a beaker. Then, 8 g (4 wt %) of Dowanol TPM (Dow) was added while stirring at 300 rpm. Mixing was continued for 10 minutes. The resulting mixture was a pourable fluid with pseudoplastic properties. A Brookfield YR-1 Rheometer was used to measure the yield stress at 0.1 rpm. The resulting Yield Stress was 12.7 Pa. The formulation was then tested for sedimentation stability according to Example 29. After 7 days, a clear layer with a thickness equal to 3% of the original column height was observed.

Example 31: Stabilizing the Formulation with THIXCIN® R (Elementis Specialties)

The agricultural formulation prepared according to Example 28 was used for the following experiment. 200 g of the agricultural formulation was added to each of three beakers. Then, sufficient THIXCIN® R (Elementis Specialties) was added to each beaker to achieve ThIXCIN® R concentrations of 0.05 wt %, 0.1 wt %, or 0.3 wt % while stirring at 300 rpm. Mixing was continued for 10 minutes while heating at 60° C. Upon cooling to room temperature, the resulting mixtures were pourable fluids with pseudoplastic properties. All formulations were tested for sedimentation stability according to Example 29. After 7 days, no sedimentation was observed in any of the formulations tested.

Example 32: Formulation Preparation

An agricultural formulation was prepared as a concentrate, in small batch sizes (small ≤250 g), using the reagents in amounts set forth below in Table 16:

TABLE 16

| Component | wt % | wt (g) |
|---|---|---|
| RLO | 54.05 | 43.24 |
| Jarfactant 325N | 2.0 | 1.60 |

TABLE 16-continued

| Component | wt % | wt (g) |
|---|---|---|
| Span 85 | 2.0 | 1.60 |
| Water | 2.5 | 2.00 |
| Bentonite | 38.2 | 30.56 |
| HPMC | 0.25 | 0.20 |
| Break Thru SP 133 | 1.00 | 0.80 |
| TOTAL | 100 | 80.00 |

To prepare the above formulations, first proper amounts of HPMC and Bentonite respectively were weighed into a sealable container; this container was then sealed and shaken to promote homogeneity. Appropriate amounts of water and Jarfactant 325N were then combined in a beaker and agitated to promote the dissolution of Jarfactant 325N. After agitation, the RLO was added, and an appropriate amount of Break-Thru SP 133 and Span 85 were added to the sample, as well. All liquid reagents were then mixed thoroughly on the laboratory overhead mixer with small fan blade attachment before that mixture was combined with the solids. The solid material was added gradually with a spatula while the mixture was stirring; once all solids had been added, a timer for 10 min was started, and the walls of the beaker (also stirring shaft) were scraped with a spatula to prevent any chunks of clay from remaining unmixed.

EQUIVALENTS

While specific embodiments of the subject invention have been disclosed herein, the above specification is illustrative and not restrictive. While this invention has been particularly shown and described with references to preferred embodiments thereof, it will be understood by those skilled in the art that various changes in form and details may be made therein without departing from the scope of the invention encompassed by the appended claims. Many variations of the invention will become apparent to those of skilled art upon review of this specification. Unless otherwise indicated, all numbers expressing reaction conditions, quantities of ingredients, and so forth, as used in this specification and the claims are to be understood as being modified in all instances by the term "about." Accordingly, unless indicated to the contrary, the numerical parameters set forth herein are approximations that can vary depending upon the desired properties sought to be obtained by the present invention.

What is claimed is:

1. A method of reducing spore-based transmission of a fungal plant disease by applying to a plant surface a nontoxic agricultural formulation of a concentrated liquid suspension comprising (i) a drying oil and (ii) particulate materials comprising clay mineral particles, wherein the particulate materials are suspended in the drying oil, and further wherein the formulation forms a cured coating on the plant surface, wherein the fungal plant disease is caused by a disease-causing fungus spore, and wherein contact with the formulation interferes with the capacity of the disease-causing fungus spore to become airborne, thereby reducing spore-based transmission of the fungal plant disease; or wherein the fungal plant disease is caused by a disease-producing fungal spore, and wherein contact with the formulation interferes with the ability of the disease-producing fungal spore to germinate on the plant surface, thereby reducing spore-based transmission of the fungal plant disease.

2. The method of claim 1, wherein the clay mineral particles are bentonite mineral particles.

3. The method of claim 1, wherein the formulation is stable against phase separation.

4. The method of claim 1, wherein the drying oil is about 40% to about 99% by weight of the formulation.

5. The method of claim 1, wherein the drying oil is selected from the group consisting of linseed oil, castor oil, castor oil glycidyl ether, tung oil, poppy seed oil, grapeseed oil, safflower oil, linoleic acid, linolenic acid, oleic acid, salicornia oil, sunflower oil, evening primrose oil, perilla oil and walnut oil.

6. The method of claim 5, wherein the drying oil is linseed oil.

7. The method of claim 6, wherein the linseed oil is raw linseed oil or boiled linseed oil.

8. The method of claim 1, wherein the drying oil is a self-crosslinking oil consisting of glycerol triesters of fatty acids.

9. The method of claim 1, wherein the drying oil comprises alpha-linoleic acid, linoleic acid, or a combination thereof.

10. The method of claim 1, wherein the suspended particulates are about 0.5% to about 50% by weight of the formulation.

11. The method of claim 1, wherein the suspended particulates are durably suspended in the drying oil.

12. A method of treating a plant infection by applying to a plant surface in need thereof a nontoxic agricultural formulation of a concentrated liquid suspension comprising (i) a drying oil and (ii) particulate materials comprising clay mineral particles, wherein the particulate materials are suspended in the drying oil and further wherein the formulation forms a cured coating on the plant surface.

13. The method of claim 12, wherein the clay mineral particles are bentonite mineral particles.

14. The method of claim 12, wherein the formulation is stable against phase separation.

15. The method of claim 12, wherein the drying oil is about 40% to about 99% by weight of the formulation.

16. The method of claim 12, wherein the drying oil is selected from the group consisting of linseed oil, castor oil, castor oil glycidyl ether, tung oil, poppy seed oil, grapeseed oil, safflower oil, linoleic acid, linolenic acid, oleic acid, salicornia oil, sunflower oil, evening primrose oil, perilla oil and walnut oil.

17. The method of claim 16, wherein the drying oil is linseed oil.

18. The method of claim 17, wherein the linseed oil is raw linseed oil or boiled linseed oil.

19. The method of claim 12, wherein the drying oil is a self-crosslinking oil consisting of glycerol triesters of fatty acids.

20. The method of claim 12, wherein the drying oil comprises alpha-linoleic acid, linoleic acid, or a combination thereof.

21. The method of claim 12, wherein the suspended particulates are about 0.5% to about 50% by weight of the formulation.

22. The method of claim 12, wherein the suspended particulates are durably suspended in the drying oil.

* * * * *